(12) United States Patent
Shluzas et al.

(10) Patent No.: US 12,728,212 B2
(45) Date of Patent: Sep. 8, 2026

(54) SYSTEM AND METHOD FOR COLLECTING INJECTION INFORMATION

(71) Applicant: CREDENCE MEDSYSTEMS, INC., Menlo Park, CA (US)

(72) Inventors: Alan E. Shluzas, San Carlos, CA (US); Mina M. Leung, Mountain View, CA (US); Jeff Tillack, Foster City, CA (US); Stephen H. Diaz, Palo Alto, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 466 days.

(21) Appl. No.: 17/895,998

(22) Filed: Aug. 25, 2022

(65) Prior Publication Data

US 2023/0061799 A1 Mar. 2, 2023

Related U.S. Application Data

(60) Provisional application No. 63/237,243, filed on Aug. 26, 2021.

(51) Int. Cl.

| | |
|---|---|
| ***A61M 5/315*** | (2006.01) |
| ***A61M 5/31*** | (2006.01) |
| ***A61M 5/32*** | (2006.01) |

(52) U.S. Cl.

CPC .... *A61M 5/31568* (2013.01); *A61M 5/31515* (2013.01); *A61M 5/32* (2013.01);

(Continued)

(58) Field of Classification Search

CPC .......... A61M 5/31568; A61M 5/31515; A61M 5/3137; A61M 2205/50; A61M 2205/14;

(Continued)

(56) References Cited

U.S. PATENT DOCUMENTS 11,654,239 B2 * 5/2023 Limaye ................. A61M 5/002 604/110
2013/0310756 A1 11/2013 Richard (Continued)

FOREIGN PATENT DOCUMENTS

CN 210489897 U * 5/2020
CN 112023190 A * 12/2020 .............. A61M 5/20

(Continued)

OTHER PUBLICATIONS

PCT International Search Report and Written Opinion for International Appln. No. PCT/2022/041590, Applicant Credence Medsystems, Inc., dated Jan. 13, 2023.

(Continued)

*Primary Examiner* — Michael J Tsai
*Assistant Examiner* — Forrest B Dipert
(74) *Attorney, Agent, or Firm* — Vista IP Law Group, LLP

(57) ABSTRACT

A system for injection includes a syringe body having proximal and distal ends, a syringe interior, and a syringe flange at the proximal end thereof. The system also includes a stopper member disposed in the syringe interior. The system further includes a plunger member coupled to the stopper member and configured to be manipulated to insert the stopper member distally in the syringe interior relative to the syringe body. Moreover, the system includes a needle coupled to the syringe body at the distal end thereof. In addition, the system includes a smart flange removably coupled to the syringe body. The smart flange includes a mounting sensor to measure mounting data. The smart flange also includes a processor to analyze the mounting data to determine the presence and the type of the syringe body disposed in the smart flange.

25 Claims, 30 Drawing Sheets

(52) U.S. Cl.
CPC ....... *A61M 5/3137* (2013.01); *A61M 2205/14* (2013.01); *A61M 2205/3306* (2013.01); *A61M 2205/3317* (2013.01); *A61M 2205/3327* (2013.01); *A61M 2205/50* (2013.01)

(58) Field of Classification Search
CPC .. A61M 2205/6027; A61M 2205/6036; A61M 2205/6045; A61M 2205/6054; A61M 2039/1044; G16H 20/17
See application file for complete search history.

(56) References Cited

U.S. PATENT DOCUMENTS

2016/0015957 A1* 1/2016 Tieck .................. A61M 5/1456 604/533
2016/0030673 A1 2/2016 White
2018/0333543 A1 11/2018 Diaz
2021/0290856 A1* 9/2021 Toporek .............. A61M 5/3158

FOREIGN PATENT DOCUMENTS

WO WO 2015136564 9/2015
WO WO 2019186261 10/2019

OTHER PUBLICATIONS

Foreign OA for EP Patent Appln. No. 22777766.1-1122 dated Feb. 2, 2025.
Foreign Voluntary Amendment A for CA Patent Appln. No. 3130053 dated Feb. 20, 2024.
Foreign Response for IN Patent Appln. No. 202447021948 dated Apr. 6, 2026.
Foreign Response to OA for EP Patent Appln. No. 22777766.1 dated Jun. 4, 2025.
Foreign OA IN Appln. No. 202447021948 dated Oct. 6, 2025.
Foreign Response for EP Patent Appln. No. 22777766.1 dated Feb. 10, 2026.
Foreign Examination Report for EP Patent Appln. No. 22 777 766.1 dated Oct. 10, 2025.
Foreign OA for JP Patent Appln. No. 2024-510642 dated May 26, 2026 (with English translation).

* cited by examiner

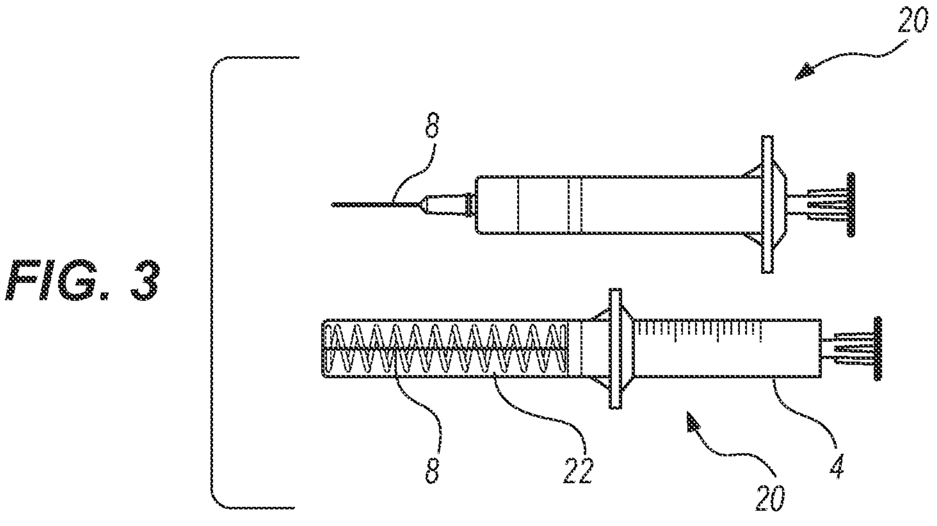
FIG. 3
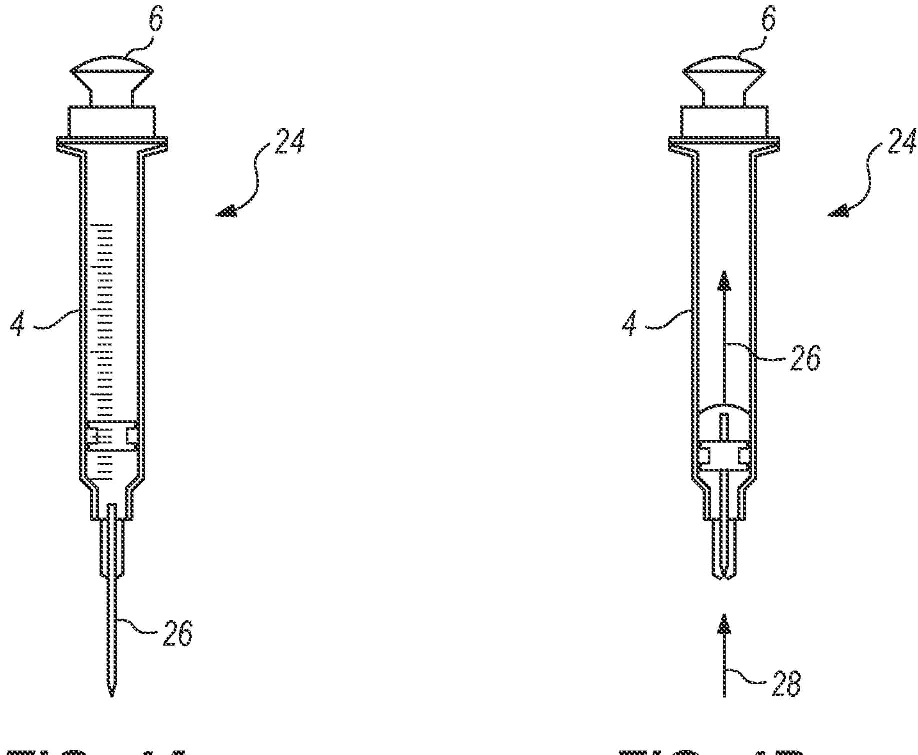
FIG. 4A
FIG. 4B

116"
126
128
112"
118"

116'
126
128
112'
118'

116
126
128
112
118

2486
2488
2480
2484
2488
2486
2250
2482
2485
2290
2216
2485
2482

SYSTEM AND METHOD FOR COLLECTING INJECTION INFORMATION

The present application claims priority to U.S. Provisional Patent Application Ser. No. 63/237,243, filed on Aug. 26, 2021 and entitled "SYSTEM AND METHOD FOR COLLECTING INJECTION INFORMATION." This application includes subject matter similar to the subject matter described in the following co-owned U.S. patent applications: (1) Ser. No. 14/696,342, filed Apr. 24, 2015, entitled "SYSTEM AND METHOD FOR SAFETY SYRINGE"; (2) Ser. No. 14/543,787, filed Nov. 17, 2014, entitled "SYSTEM AND METHOD FOR DRUG DELIVERY WITH A SAFETY SYRINGE"; (3) Ser. No. 14/321,706, filed Jul. 1, 2014, entitled "SAFETY SYRINGE"; and (4) Ser. No. 62/416,102, filed Nov. 1, 2016, entitled "SYSTEM AND METHOD FOR SAFETY SYRINGE"; (5) Ser. No. 62/431,382, filed Dec. 7, 2016, entitled "SYSTEM AND METHOD FOR SAFETY SYRINGE"; (6) Ser. No. 62/480,276, filed Mar. 31, 2017, entitled "SYSTEM AND METHOD FOR SAFETY SYRINGE"; (7) Ser. No. 15/985,354, filed May 21, 2018, entitled "SYSTEM AND METHOD FOR COLLECTING INJECTION INFORMATION"; and (8) Ser. No. 17/169,806, filed Feb. 8, 2021, entitled "SYSTEM AND METHOD FOR COLLECTING INJECTION INFORMATION." The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to safety syringes in healthcare environments. Even more particularly, the present invention relates to injection systems, devices, and processes for managing injection related information.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling.

The use of needle injection configurations, on the other hand, carries with it the risk of a sharp needle contacting or stabbing a person or structure that is not desired. For this reason, so called "safety syringes" have been developed. One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possibly malfunction and activate before desirable, loss of accuracy in giving full-dose injections due to residual dead space within the spring compression volume, and/or loss of retraction velocity control which may be associated with pain and patient anxiety. Other "safety syringes" are described in U.S. patent application Ser. Nos. 14/696,342, 14/543,787, 14/321,706, 62/416,102, 62/431,382, and 62/480,276, the contents of which have been incorporated herein by reference.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface (14). Liquid medicine may reside in the volume, or medicine reservoir, (40) between the distal seal (35) and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body (34) structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the medicine chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more “vertical” solutions, such as the system (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Automated injection information collection can lead to advancements in various healthcare areas including but not limited to, healthcare informatics, personalized medicine, electronic medical records, and personalize wearable computing devices. The collected injection information can be used to assist patients in management and scheduling of injectable medicine delivery. The collected injection information can also be sent to third party (e.g., healthcare providers, clinical/medical research organizations, pharmaceutical companies, insurers, etc.) to improve management and personalization of medical care. Real-time injection monitoring, data capture, and feedback are among the types of injection information that can be collected. Collection of such injection information can enable clinical trial remote monitoring and data integrity. Collection of such injection information can also enable improved compliance to achieve cost containment. Collection of such injection information can further enable focus messaging to user cohorts. Moreover, collection of such injection information can enable characterization of use patterns and improved disease management.

Regardless of the type of injection system, collecting information relating to the delivery of injectables (e.g., medications) can provide many advantages. In embodiments where injectable medications are self-administered by patients, collecting information relating to the delivery of injectables (i.e., “injection information”) can facilitate determination of patient compliance. In such embodiments, the injection information may include injection timing, whether the injection has been delivered, and/or the size/dose of the injection. Because patient noncompliance increases the cost of healthcare, determining patient compliance can reduce healthcare costs and improve healthcare results. Even in embodiments where injectable medications are administered by medical professionals, collecting injection information can increase the tracking accuracy for injectable medication delivery, which in turn reduces healthcare costs and improves healthcare results (e.g., by determining whether an injection was properly delivered). Automating the collection of injection information can secure these and many other advantages with minimal or no human intervention.

In the exemplary case of treatment and management of diabetes, the millions of Americans affected by diabetes take a variety of injectable medications, including injectable insulin. However, injectable insulin includes various risks such as difficulty in titrating appropriate dosage, which may result in under-treatment or hypoglycemia. Despite these risks, roughly 10,000,000 Americans take insulin daily to manage their diabetes. Insulin is administered in three primary ways: syringe, pen, and pump. Vials and syringes are the most cost effective insulin administration modality. Collection of injection information specifically for injection of insulin can reduce the risks associated with injectable insulin. Insulin injection information can also be used to manage treatment of diabetes as part of a digital/virtual diabetes clinic. Patient care can be improved with collection of behavioral, contextual, and real-time data; predictive analytics and adaptive learning; and mobile engagement and feedback.

There is a need for injection systems which address the shortcomings of currently-available configurations. In particular, there is a need for injection system that may automatically collect injection information while utilizing the existing and relatively well-controlled supply chain of conventionally delivered syringes and cartridges. Further, there is a need for injection systems that may communicate with various stakeholders (e.g., patients, healthcare providers, clinical/medical research organizations, pharmaceutical companies, insurers, etc.) based on collected injection information to improve healthcare results and reduce healthcare costs.

SUMMARY

Embodiments are directed to injection systems. In particular, the embodiments are directed to safe injection systems that collect information relating to the delivery of injectables.

In one embodiment, a system for injection includes a syringe body having proximal and distal ends, a syringe interior, and a syringe flange at the proximal end thereof. The system also includes a stopper member disposed in the syringe interior. The system further includes a plunger member coupled to the stopper member and configured to be manipulated to insert the stopper member distally in the syringe interior relative to the syringe body. Moreover, the system includes a needle coupled to the syringe body at the distal end thereof. In addition, the system includes a smart flange removably coupled to the syringe body. The smart flange includes a mounting sensor to measure mounting data corresponding to a presence and a type of the syringe body disposed in the smart flange. The smart flange also includes a processor to analyze the mounting data to determine the presence and the type of the syringe body disposed in the smart flange.

In one or more embodiments, the mounting sensor includes a contact member extending into a mounting space defined by the smart flange. The mounting sensor may also include a mounting elongate member, wherein the contact member is coupled to a middle portion of the mounting elongate member. The mounting sensor may further include a mounting magnetic member coupled to a distal end of the mounting elongate member. Moreover, the mounting sensor may include a mounting magnetic sensor disposed adjacent the mounting magnetic member.

In one or more embodiments, the contact member and the smart flange are configured such that disposing the syringe body in the mounting space of the smart flange moves the contact member relative to the smart flange. The mounting elongate member and the contact member may be configured such that moving the contact member relative to the smart flange elastically deforms the mounting elongate member. The mounting magnetic member and the mounting elongate member may be configured such that elastically deforming the mounting elongate member moves the mounting magnetic member relative to the mounting magnetic sensor. The mounting magnetic sensor may detect movement of the mounting magnetic member and generate the mounting data based on the detected movement of the mounting magnetic member.

In one or more embodiments, the mounting magnetic sensor is a magnetoresistive angle sensor. The smart flange may define an internal space, and the mounting elongate member, the mounting magnetic member, and the mounting magnetic sensor may be disposed in the internal space.

In one or more embodiments, the smart flange further includes an injection sensor to measure injection data corresponding to a movement of the plunger member relative to the syringe body. The processor may analyze the injection data to determine an occurrence of an injection event. The injection sensor may include a wheel, an injection elongate member coupled to the wheel and rotatably mounted to the smart flange, an injection magnetic member coupled to a distal end of the elongate member, and an injection magnetic sensor disposed adjacent the magnetic member. The smart flange may define an internal space, and the injection elongate member, the injection magnetic member, and the injection magnetic sensor may be disposed in the internal space. The wheel may be the contact member. The injection elongate member may be the mounting elongate member. The injection magnetic member may be the mounting magnetic member. The injection magnetic sensor may be the mounting magnetic sensor.

In one or more embodiments, the wheel and the smart flange are configured such that moving the plunger member axially relative to the smart flange rotates the wheel. The injection elongate member and the wheel may be configured such that rotating the wheel rotates the injection elongate member. The injection magnetic member and the injection elongate member may be configured such that rotating the injection elongate member rotates the injection magnetic member relative to the injection magnetic sensor. The injection magnetic sensor may detect rotation of the injection magnetic member and generates the injection data based on the detected rotation of the injection magnetic member. The injection magnetic sensor may be a magnetoresistive rotary sensor.

In one or more embodiments, the plunger member has an X-shaped cross-section and includes four radially extending portions. The wheel and the plunger member may be configured such that the wheel contacts two of the four radially extending portions of the plunger member.

In one or more embodiments, the injection sensor includes a roller rotatably mounted to the smart flange, an injection magnetic member coupled to a distal end of the roller, and an injection magnetic sensor disposed adjacent the injection magnetic member. The smart flange may define an internal space, and the injection elongate member, the injection magnetic member, and the injection magnetic sensor may be disposed in the internal space. The roller and the smart flange may be configured such that moving the plunger member axially relative to the smart flange rotates the roller. The injection magnetic member and the roller may be configured such that rotating the roller rotates the injection magnetic member relative to the injection magnetic sensor. The injection magnetic sensor may detect rotation of the injection magnetic member and generate the injection data based on the detected rotation of the injection magnetic member. The injection magnetic sensor may be a magnetoresistive rotary sensor.

In one or more embodiments, the plunger member has an X-shaped cross-section and includes four radially extending portions. The roller and the plunger member may be configured such that the roller contacts two of the four radially extending portions of the plunger member. The smart flange may include a pair of orientation ribs defining a mounting space sized to allow the smart flange to mount on the plunger member only with roller in contact with two of the four radially extending portions of the plunger member. The roller may be suspended in the smart flange to accommodate a plurality of syringe bodies having respective different sizes.

In one or more embodiments, the injection sensor includes a wheel and an injection sensor disposed adjacent the wheel to measure a rotation of the wheel. The injection sensor may be an optical sensor and/or a capacitive sensor. The syringe body may include a syringe flange, and the smart flange may include a plurality of snaps configured to releasably couple the smart flange to the syringe body. The syringe body may have a volume selected from the group consisting of 0.3 ml, 0.5 ml, and 1 ml. The syringe body may have any other volume, such as 2.25 ml, 3 ml, or 5 ml. The plunger member may have an X-shaped cross-section. The smart flange may define a side-facing mounting opening, and the smart flange may include a pair of orientation ribs configured to orient the plunger member as it enters the side-facing mounting opening.

In another embodiment, a system for injection includes a syringe body having proximal and distal ends, a syringe interior, and a syringe flange at the proximal end thereof. The syringe body also includes a stopper member disposed in the syringe interior. The syringe body further includes a plunger member coupled to the stopper member and configured to be manipulated to insert the stopper member distally in the syringe interior relative to the syringe body. Moreover, the syringe body includes a needle coupled to the syringe body at the distal end thereof. In addition, the syringe body includes a smart flange removably coupled to a syringe body. The smart flange includes an injection sensor to measure injection data corresponding to a movement of the plunger member relative to the syringe body. The smart flange also includes a processor to analyze the injection data to determine an occurrence of an injection event.

In one or more embodiments, the injection sensor includes first and second rollers rotatably mounted to the smart flange. The injection sensor may also include first and second rotor disks coupled to respective first and second rollers. The injection sensor may further include first and second capacitive sensors disposed adjacent the first and second rotor disks. The first and second rollers may each include a mandrel covered with an elastic material. The injection sensor may further include a U-shaped member threaded through respective mandrels of the first and second rollers. The U-shaped member may be configured to apply a biasing force moving the respective mandrels of the first and second rollers toward each other when the respective mandrels of the first and second rollers are moved away from each other. The first and second rotor disks may each include a plurality of metal pads. The first and second capacitive sensors may each include a stator.

In one or more embodiments, the processor is configured to apply a high frequency current to each of the capacitive sensors. The injection sensor may further include a first dielectric member disposed between the first rotor disk and the first capacitive sensor, and a second dielectric member disposed between the second rotor disk and the second capacitive sensor. The injection sensor may further include a third capacitive sensors disposed adjacent the first rotor disk opposite of the first capacitive sensor, and a fourth capacitive sensors disposed adjacent the second rotor disk opposite of the second capacitive sensor. The first and second rollers may be movable relative to the smart flange.

In one or more embodiments, the system further includes a mounting sensor to measure mounting data corresponding to a presence and a type of the syringe body disposed in the smart flange, and the processor analyzes the mounting data to determine the presence and the type of the syringe body disposed in the smart flange. The mounting sensor may include a contact member coupled to the first roller, and a contact detector disposed adjacent the contact member such that deforming the first roller away from the second roller places the contact member in contact with the contact detector.

In still another embodiment, a method for determining an amount of an injectable fluid ejected from an injection system includes attaching a syringe body to a smart flange. The method also includes detecting and storing a first position of a plunger member in the syringe body relative to the smart flange after the syringe body is attached to the smart flange and before the plunger member is moved. The method further includes detecting and storing a second position of the plunger member relative to the smart flange after the plunger member is moved proximally from the first position to draw air into the syringe body. Moreover, the method includes detecting and storing a third position of the plunger member relative to the smart flange after the plunger member is moved distally from the second position to inject at least some of the air into a vial of injectable fluid. In addition, the method includes saving the third position of the plunger member as a baseline/zero position of the plunger member. The method also includes detecting and storing a fourth position of the plunger member relative to the smart flange after the plunger member is moved proximally from the third position to draw at least some of the injectable fluid and some air into the syringe body. The method further includes detecting and storing a fifth position of the plunger member relative to the smart flange after the plunger member is moved distally a small amount from the fourth position to expel some air from the syringe body. Moreover, the method includes calculating a volume of the injectable fluid in the syringe body from the fifth position of the plunger member relative to the smart flange and the baseline/zero position of the plunger member.

In one or more embodiments, the third position of the plunger member relative to the smart flange corresponds to a position of a stopper member coupled to the plunger member at a distal end of the syringe body. The method may further include communicating the volume of injectable fluid in the syringe body to a user. Communicating the volume of injectable fluid may be selected from the group consisting of displaying the volume of injectable fluid and playing an audio indicator of the volume of injectable fluid. The method may further include indicating to a user when the volume of injectable fluid in the syringe body is equal to a predetermined volume of injectable fluid. The method may further include indicating to a user when the volume of injectable fluid in the syringe body is larger than a predetermined volume of injectable fluid.

In yet another embodiment, a system for injection includes a syringe body having proximal and distal ends, a syringe interior, and a syringe flange at the proximal end thereof. The system also includes a stopper member disposed in the syringe interior. The system further includes a plunger member coupled to the stopper member and configured to be manipulated to insert the stopper member distally in the syringe interior relative to the syringe body. Moreover, the system includes a needle coupled to the syringe body at the distal end thereof. In addition, the system includes a smart flange removably coupled to a syringe body. The smart flange includes a drive wheel to move the plunger member along a longitudinal axis, a motor to rotate the drive wheel, and an idler wheel to urge the plunger member against the drive wheel.

The smart flange may be utilized with syringes which are pre-filled with medicine by the manufacturer and/or syringes which are filled by the user prior to giving the injection. In both cases, the smart flange may come pre-mounted onto the syringe or be mounted to the syringe at the time of the injection. Additionally, the some or all of the smart flange electronic components and sensors may be located in or on the plunger rod.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 1A-1B, 2A-2B, 3, 4A-4B, and 5A-5C illustrate various aspects of conventional injection syringe configurations.

FIG. 24 is a perspective view. FIGS. 25 and 26 are exploded views. FIG. 27 is a cross-sectional view.

Figure 1A:
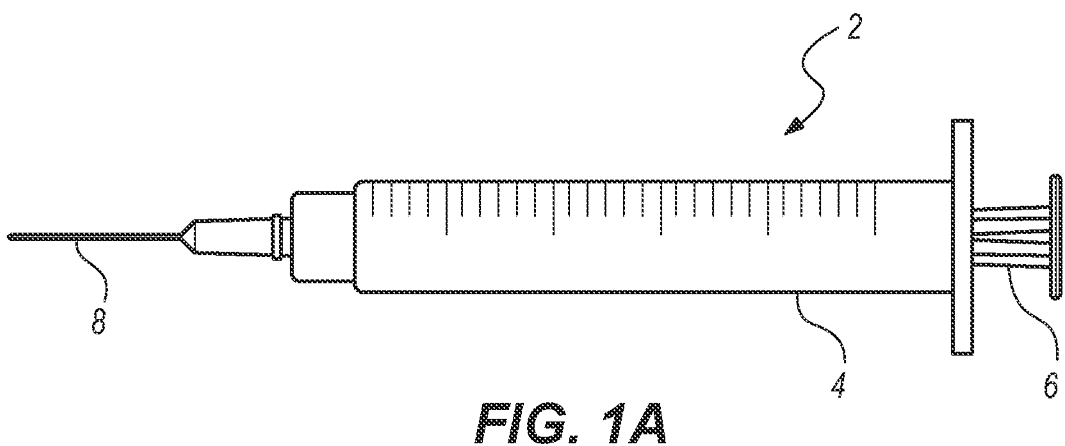
Figure 1B:
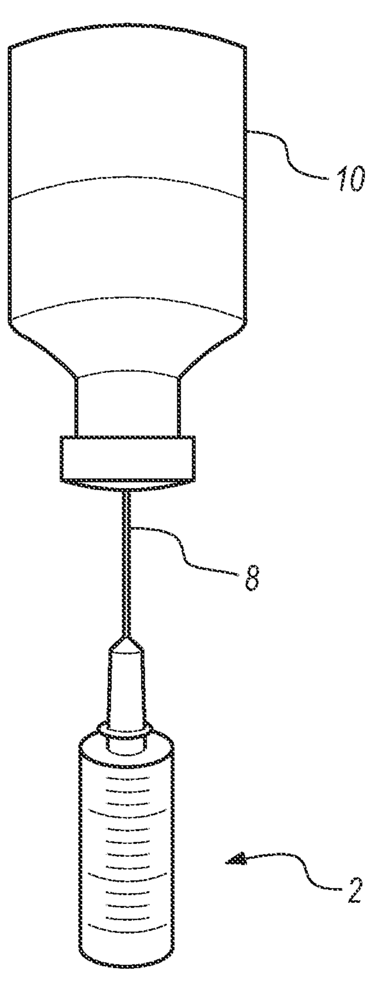
Figure 2A:
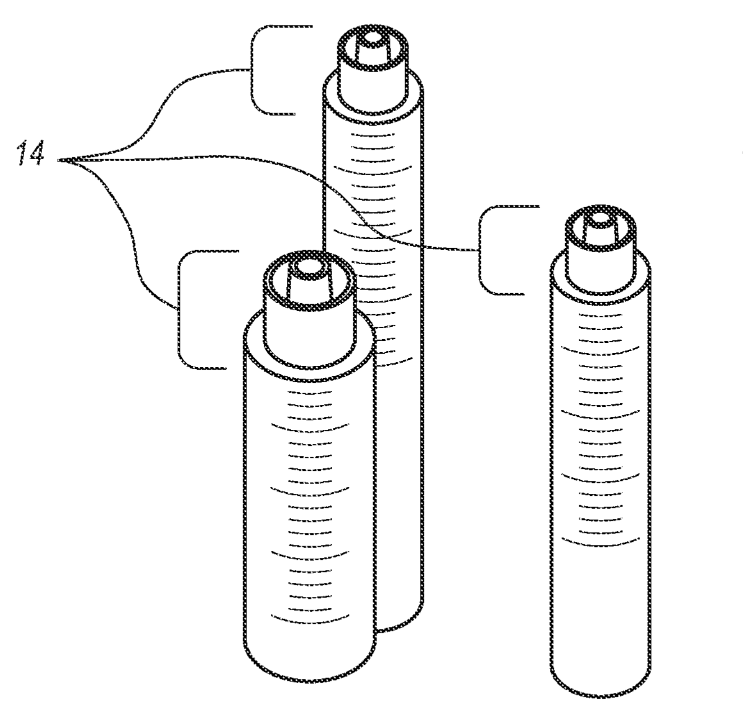
Figure 2B:
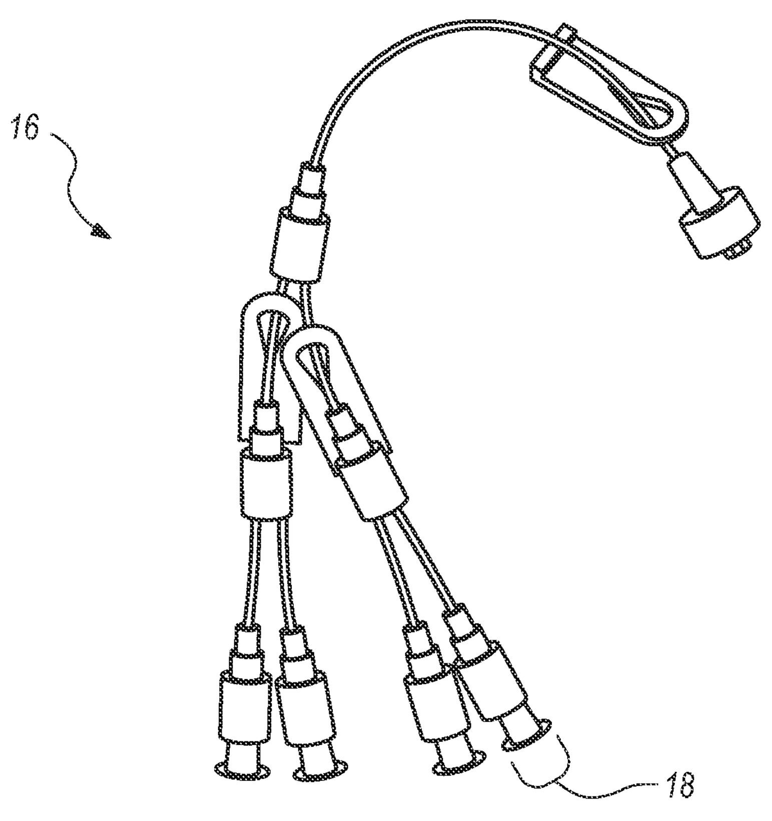
Figure 5A:
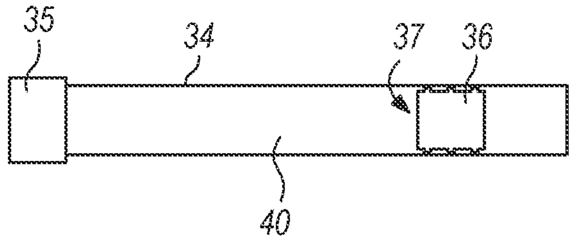
Figure 5B:
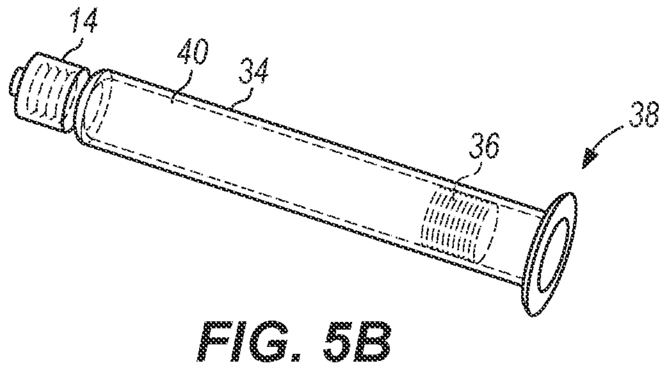
Figure 5C:
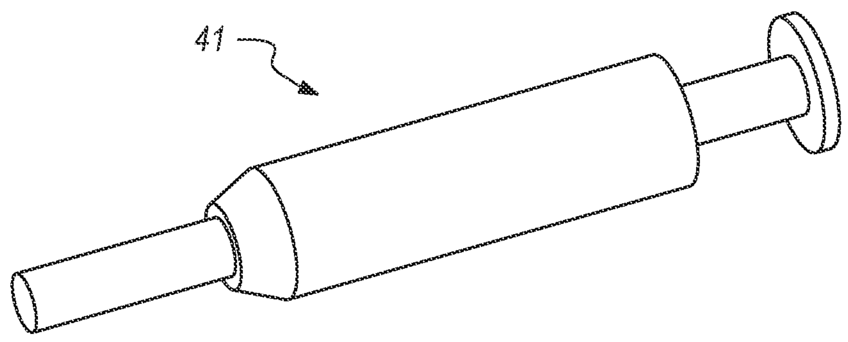

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Injection Systems with Smart Flanges and Smart Injection Methods

Figure 6:
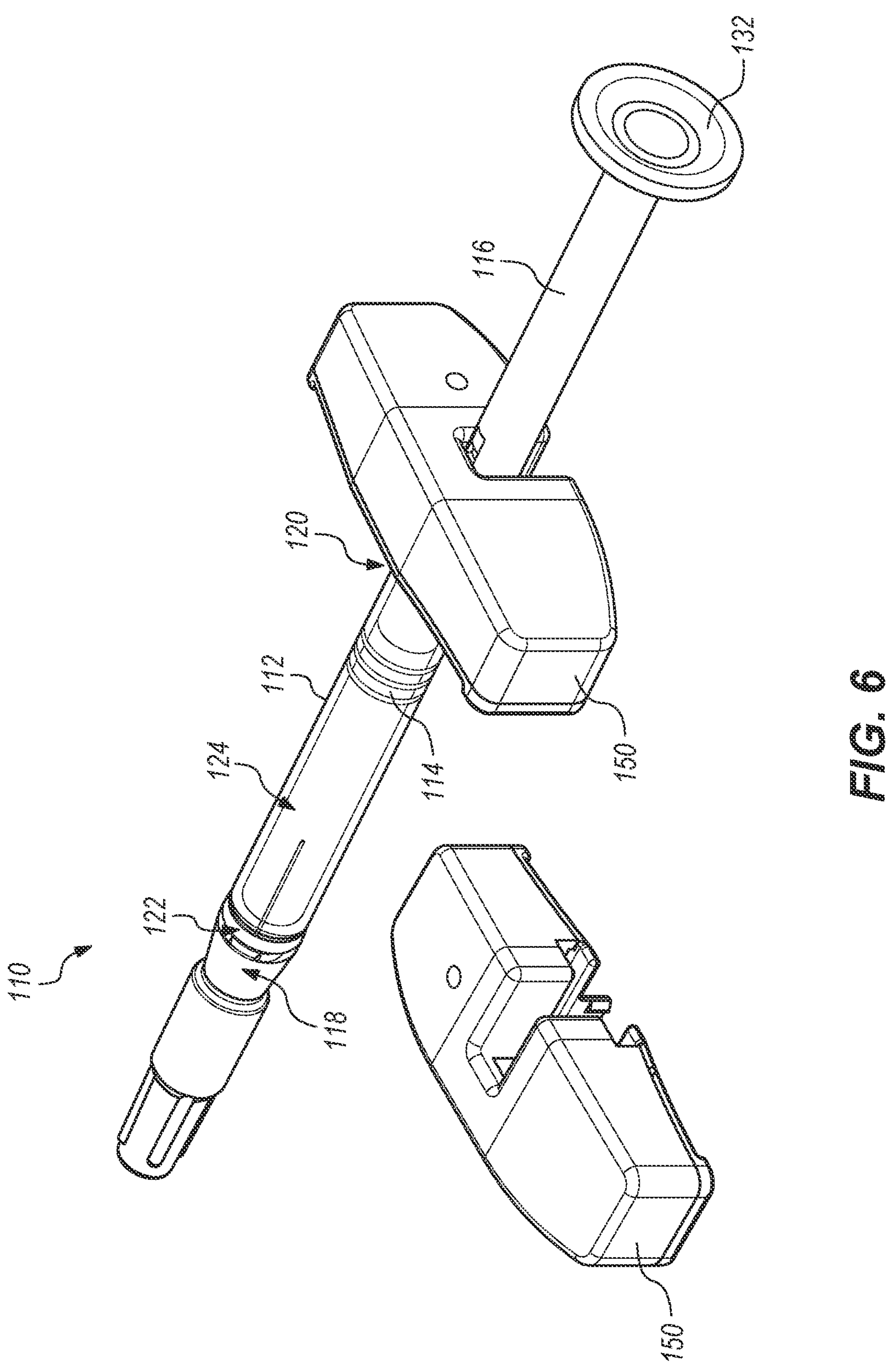
FIG. 6 illustrates a smart flange separated from and removably coupled to a syringe according to some embodiments.

Referring to FIG. 6, an injection system (110) includes a syringe body (112), a stopper member (114), a plunger member (116), a needle assembly (118), and a smart flange (150) removably attached to the syringe body (112). The syringe body (112) includes an open proximal end (120) and an open distal end (122). The syringe body (112) also includes a syringe interior (124), a syringe flange (126, see FIGS. 7A to 7C) at the proximal end (120) thereof. The stopper member (114) is disposed in the syringe interior (124), and coupled to the plunger member (116), such that the plunger member (116) may be manipulated to insert the stopper member (114) distally into the syringe interior (124) to expel an injectable substance (e.g., fluid) from the syringe interior (124) through the needle assembly (118). The needle assembly (118) may include a needle coupling member at a proximal end thereof or the needle assembly (118) may be staked to the syringe body (112). The plunger member (116) includes a proximal end pad (132) to facilitate manual manipulation of the plunger member (116) using a digit (e.g., a thumb) of a user's hand while one or more other digits of the user's hand provide an opposing force (e.g., against a distal side of the syringe flange (126) or a smart flange (150) disposed thereon).

Figures 7A, 7B, 7C:
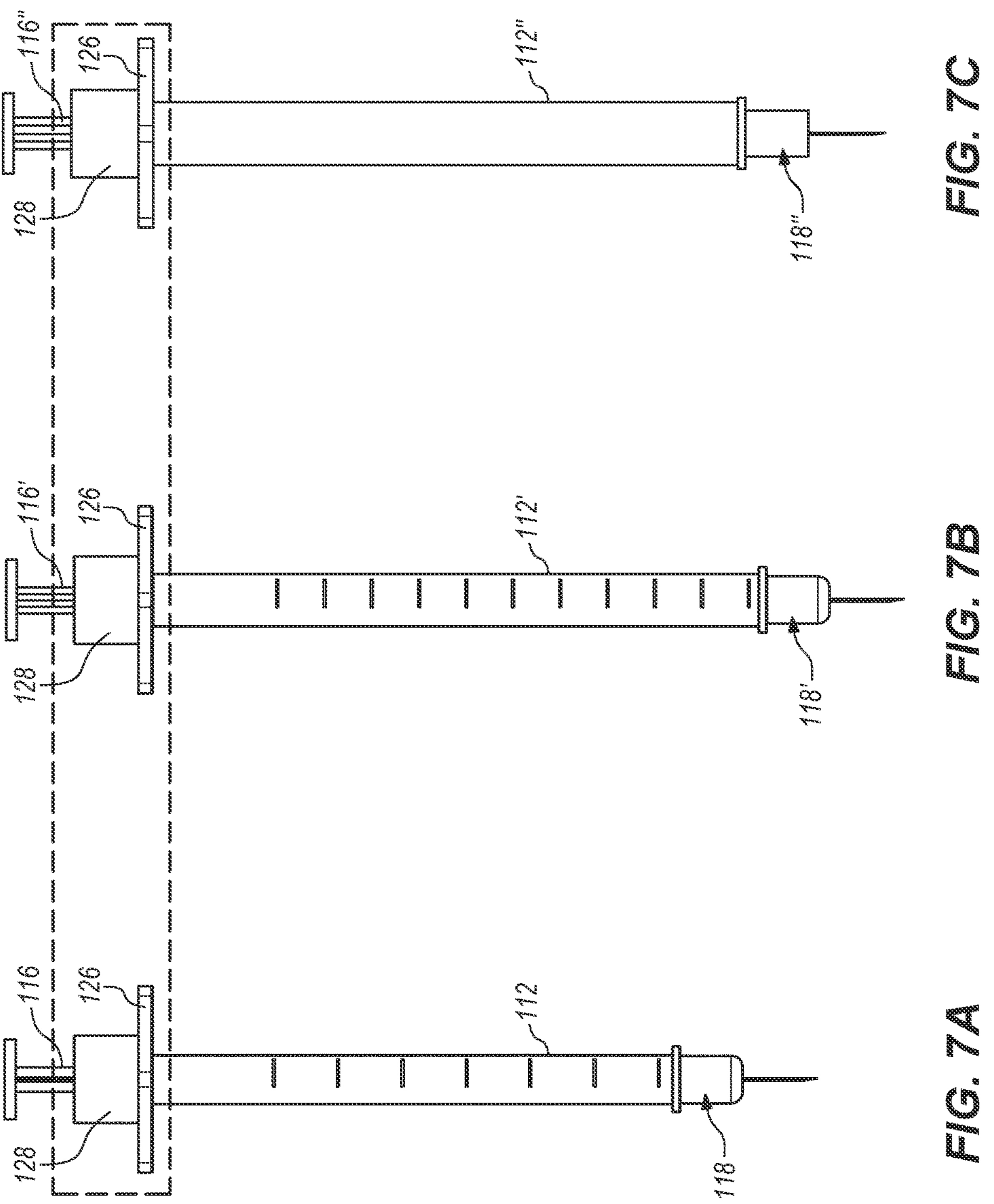
FIGS. 7A to 7C illustrate three syringes of different sizes for use with a smart flange according to some embodiments.

FIGS. 7A to 7C depict three syringe bodies (112, 112', 112") of different sizes for use with a smart flange (150, see FIG. 6) according to some embodiments. FIG. 7A depicts a syringe body (112) with a volume of 0.3 ml. the syringe body (112) has an outer diameter of approximately 0.204" and the plunger member (116) has an outer diameter of approximately 0.104" to conform to the syringe body (112). FIG. 7B depicts a syringe body (112') with a volume of 0.5 ml. the syringe body (112') has an outer diameter of approximately 0.226" and the plunger member (116') has an outer diameter of approximately 0.122" to conform to the syringe body (112'). FIG. 7C depicts a syringe body (112") with a volume of 1 ml. the syringe body (112") has an outer diameter of approximately 0.267" and the plunger member (116") has an outer diameter of approximately 0.168" to conform to the syringe body (112"). The needle assemblies (118, 118', 118") depicted in FIGS. 7A to 7C may also have slightly different proximal ends to conform to syringe bodies (112, 112', 112"). In other embodiments, the syringe body may have any other volume, such as 2.25 ml, 3 ml, or 5 ml. Regardless of the size of the syringe bodies (112, 112', 112"), the syringe flange (126) and a proximal end member (128) of each of the syringe bodies (112, 112', 112") have the same geometry in order to facilitate attachment of the smart flange (150, see FIG. 6).

Figure 8:
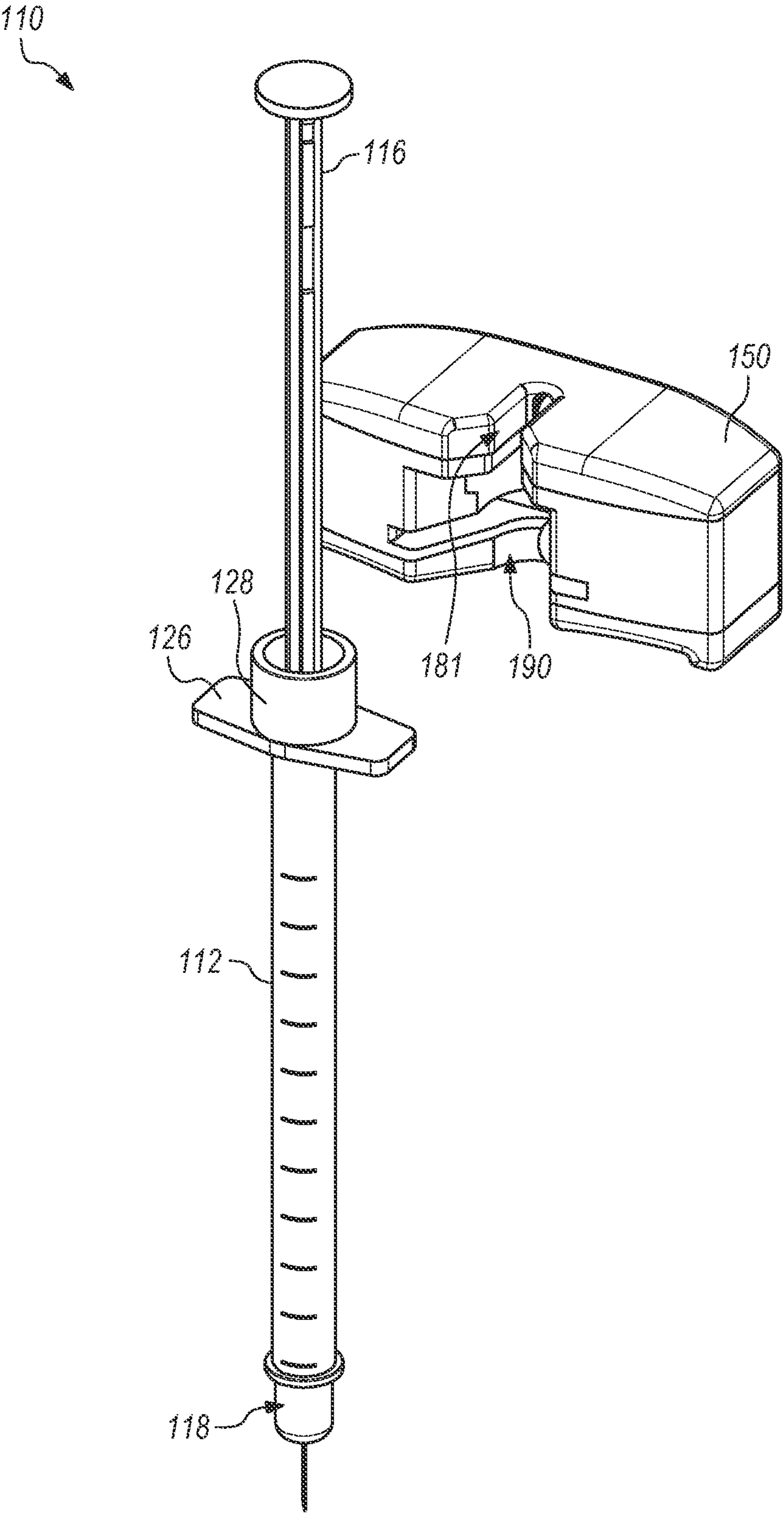
FIG. 8 illustrates a smart flange and a syringe to which the smart flange can be removably coupled according to some embodiments.

The smart flange (150) is depicted in FIG. 8 before it is removably coupled to the syringe body (112). The smart flange (150) depicted in FIG. 8 is designed to clip/snap onto the syringe body (112) around the syringe flange (126) and the proximal end member (128). A user can snap a mounting opening/notch (190) defined by the smart flange (150) onto the syringe flange (126) and the proximal end member (128) of the syringe body (112). Because the syringe flange (126) and the proximal end member (128) can be the same in syringe bodies (112, 112', 112", see FIGS. 7A to 7C) with different volumes, the smart flange (150) can removably couple to syringe bodies regardless of their volumes. This aspect allows the smart flange (150) to be used with a wide variety of syringe bodies (112) available in existing supply chain of conventional injection system components.

Figure 9:
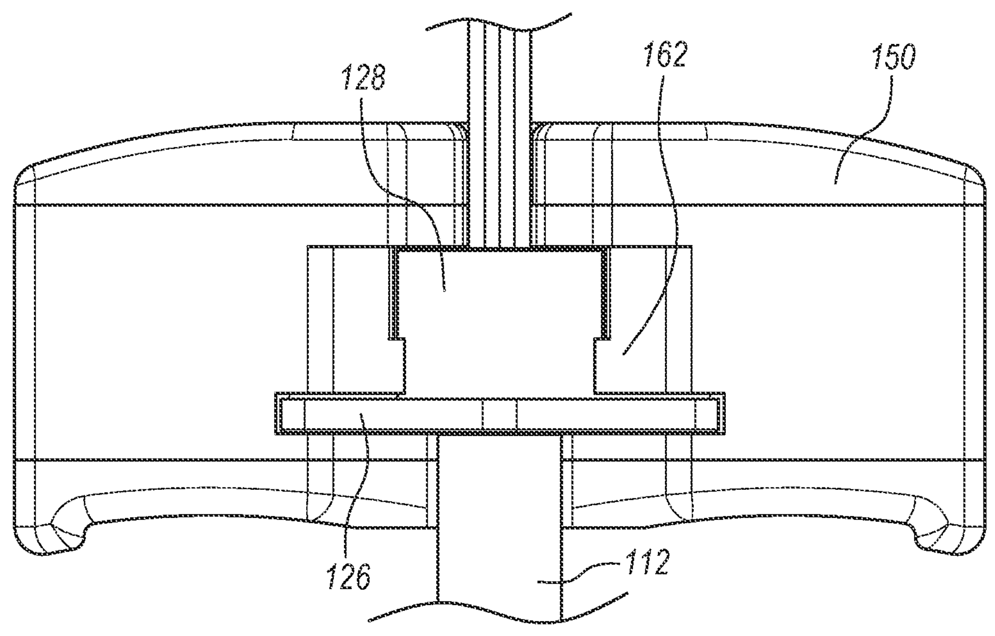
FIG. 9 illustrates a smart flange removably coupled to a syringe according to some embodiments.

FIG. 9 depicts the smart flange (150) after it has been removably coupled to the syringe body (112). The smart flange (150) includes a pair of snaps (162) configured to elastically deform around the proximal end member (128) of the syringe body (112) as the smart flange (150) is slid onto the syringe flange (126) and the proximal end member (128) of the syringe body (112), as shown in FIG. 8.

Figure 10A:
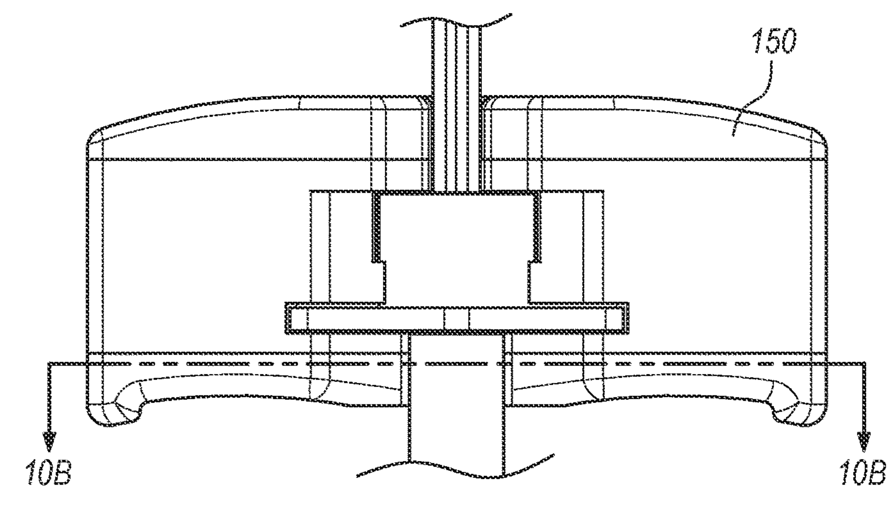
FIGS. 10A and 10B illustrate a smart flange before it is removably coupled to a syringe according to some embodiments.
Figure 10B:
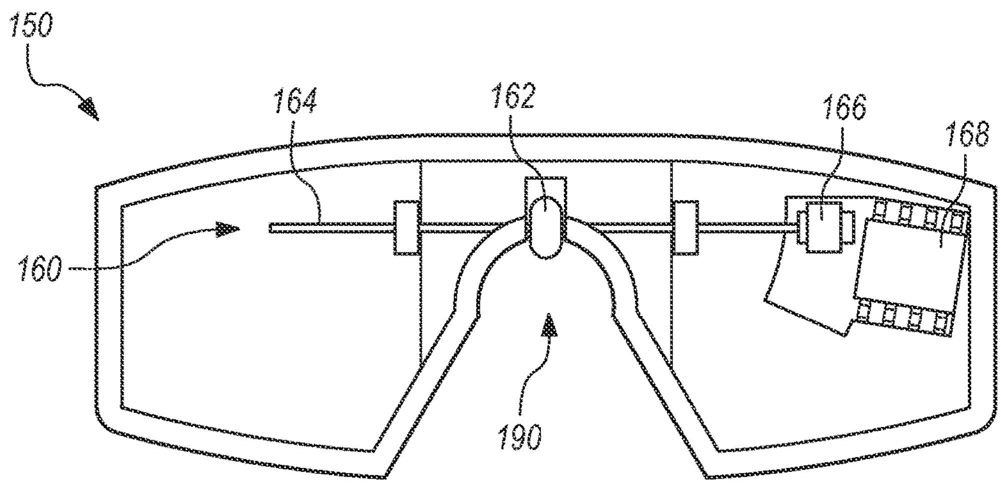

FIG. 10A depicts the level of the cross-sectional view of FIG. 10B in the smart flange (150). As shown in FIG. 10B, according to some embodiments, the smart flange (150) has a mounting sensor (160) disposed therein. The mounting sensor (160) is configured to measure mounting data corresponding to a presence and a type (e.g., size) of the syringe body to which the smart flange (150) is mounted. FIG. 10B depicts a smart flange (150) before it is mounted to any syringe body. The mounting sensor (160) includes a contact member (162), which extends partially into the mounting opening/notch (190) defined by the smart flange (150). The mounting sensor (160) also includes a mounting elongate member (164) to which the contact member (162) is coupled. The mounting elongate member (164) may be a metal wire or rod configured to elastically deform with force applied through the contact member (162) coupled to a middle portion thereof. In some embodiments, the contact member (162) may have an opening through which the mounting elongate member (164) may be threaded. In such embodiments, the contact member (162) is slidably coupled to the mounting elongate member (164), but movements of the contact member (162) into and out of the mounting opening/notch (190) will still elastically deform the mounting elongate member (164). The mounting sensor (160) further includes a mounting magnetic member (166) coupled to a distal end of the mounting elongate member (164). Moreover, the mounting sensor (160) includes a magnetic sensor (168) disposed adjacent the mounting magnetic member (166). The magnetic sensor (168) may be a magnetoresistive angle sensor. Magnetoresistive angle sensors are useful in this type of mounting sensor (160) because they have higher sensitivity in this application than other types of magnetic sensor such as Hall Effect sensors. Additionally, magnetoresistive sensors are omni-polar (i.e., operates with North and South poles). Wherein, hall effect sensors operate with either a North or a South pole. Operating in omni-polar mode allows the magnetoresistive sensor to operate with higher precision in this application as the signal from the moving magnetic field is doubled, because the sensor responds to movement of both the North and South poles.

Figure 10C:
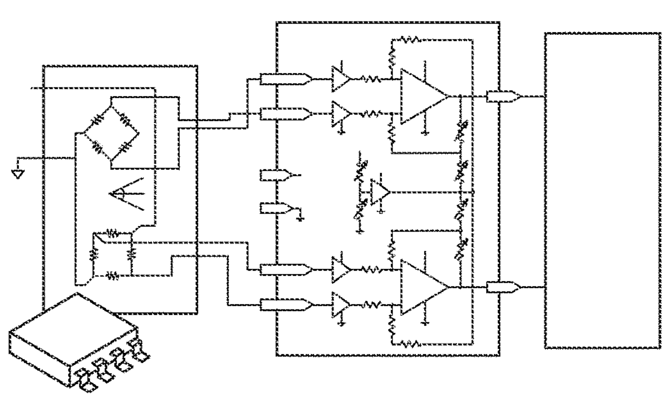
FIGS. 10C and 10D schematically depict a commercially available magnetoresistive sensor according to some embodiments.
Figure 10D:
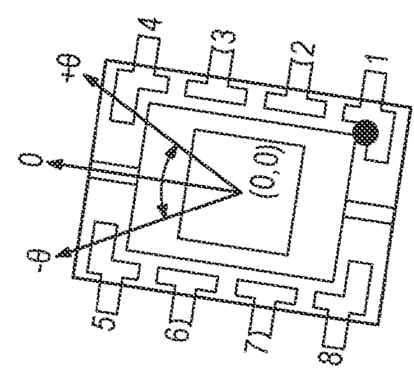

FIGS. 10C & 10D schematically depict a commercially available magnetoresistive sensor according to some embodiments. One of the major uses for magnetoresistive sensors is for precision, non-contact measurement of displacement. An example of such a sensor is the APS00B from Honeywell Sensing and Control. The APS00B high-resolution magnetic angular-position sensor IC is a miniature surface-mounted device for measuring angular or rotary displacement designed for magnetic, saturating field sensing. The magnetoresistive sensor creates an analog output voltage that varies with the direction of the magnetic flux passing over the integrated circuit (IC) surface.

The APS00B uses Honeywell's Anisotropic Magnetoresistive (AMR) technology, which has some advantages over Hall Effect based magnetic sensors. AMR is able to resolve better than a tenth of a degree and/or a tenth of a millimeter, withstand large variations in magnet-to-sensor gaps, and exhibit insensitivity to shocks and vibrations. The technology is used in dual saturated-mode Wheatstone bridges that generate quadrature (sine and cosine) signals to provide an extended range of angular measurements up to 180°.

Installation of the flange on to the syringe causes the contact member (162) to be moved by the plunger rod (112). Movement of the contact member (162) bends the elongate member (164). The bend defines a bend plane. The magnetoresistive sensor disclosed in figures A, B, and C is designed to respond to magnetic fields parallel to the sensor mounting plane. In this case the sensor mounting plane is parallel to the bend plane, which allows the magnetoresistive sensor to detect movement of the magnet in the bend plane corresponding to the amount of bend applied to the elongate member. A magnetoresistive sensor is good at unipolar sensing for precision, non-contact of displacement applications such as medical analyzers and magnetic field encoders. In an alternative embodiment both the angular position sensor (108) and an angular rotation sensor may be used. The magnetic rotation sensor as shown in FIG. 12B may be located on the other end of the elongate member (164) and used in conjunction with an angular position sensor. Other encoding and/or angle sensing technologies which could be incorporated into the device are: optical encoders, hall effect sensors, Tunneling Magnetoresistance (TMR) sensors, accelerometers, flange orientation sensor, flange tip sensors, gyroscopic position sensors, inertial motion unit sensors, capacitive encoders, inductive encoder, mechanical encoder, incremental encoder, commutative encoder, and/or a series of mechanical switches oriented to form a rotary encoder.

Figure 11A:
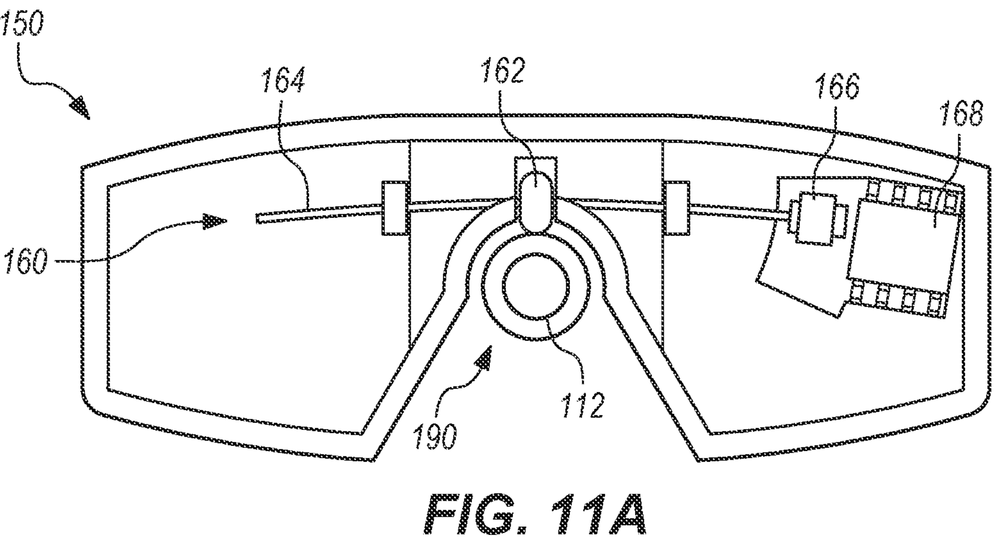
FIGS. 11A to 11C illustrate a smart flange removably coupled to syringes of various sizes according to some embodiments.
Figure 11B:
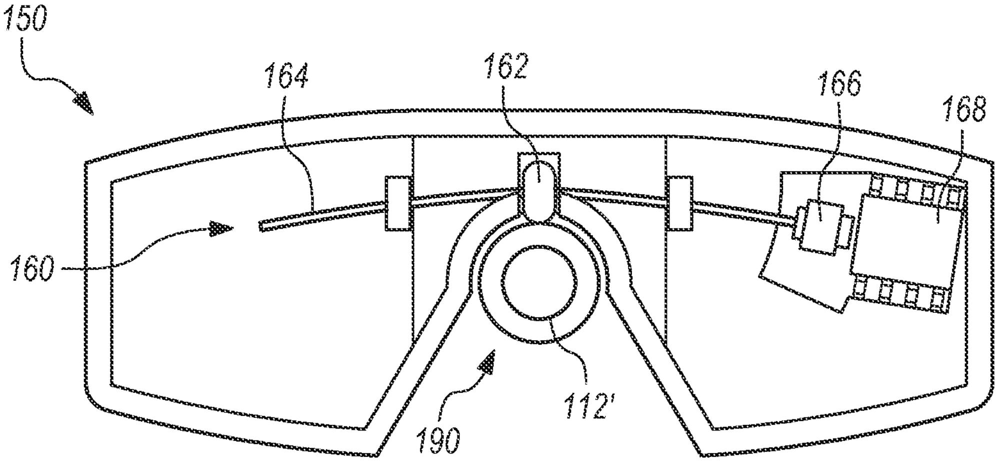
Figure 11C:
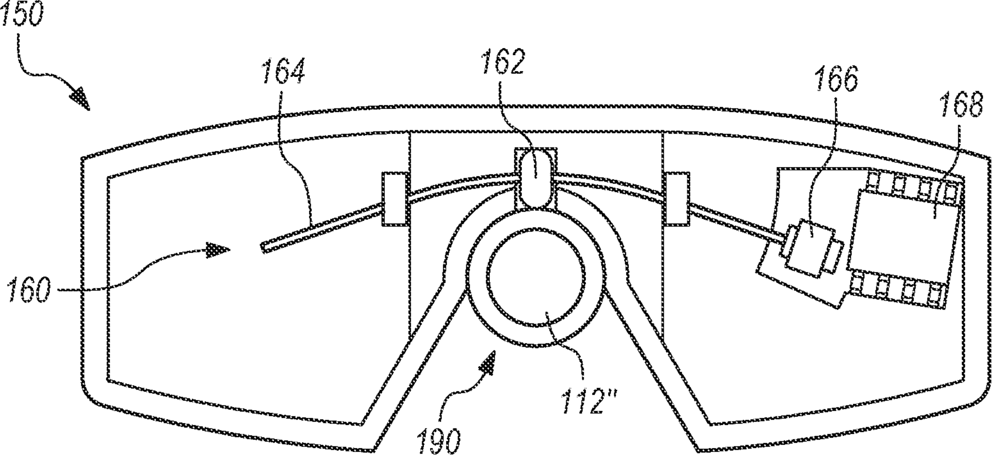

FIGS. 11A, 11B, and 11C depict the smart flange (150) mounted onto syringe bodies (112, 112', 112") having volumes of 0.3 ml 0.5 ml, and 1 ml, respectively. The level of the cross-sectional views of FIGS. 11A, 11B, and 11C is the same as the level of FIG. 10B as depicted in FIG. 10A. As the volumes and the corresponding radii of the syringe bodies (112, 112', 112") increases, the contact member (162) in contact with the respective syringe bodies (112, 112', 112") is pushed further into the smart flange (150) by the respective syringe bodies (112, 112', 112"). As the contact member (162) is pushed further into the smart flange (150) by the increasing radii of the respective syringe bodies (112, 112', 112"), the mounting elongate member (164) is more deformed by the contact member (162) with the middle of the mounting elongate member (164) push further into the smart flange (150). As the mounting elongate member (164) is more deformed by the contact member (162), the mounting magnetic member (166) is moved further toward the respective syringe bodies (112, 112', 112") as shown in FIGS. 11A, 11B, and 11C. The mounting magnetic sensor (168) detects the position of the mounting magnetic member (166) as it moves relative to the mounting magnetic sensor (168).

The mounting magnetic sensor (168) generates mounting data corresponding to the relative position of the mounting magnetic member (166). The smart flange (150) includes a processor to analyze the mounting data to determine the presence and type (e.g., size) of the syringe body (112, 112', or 112") to which the smart flange (150) is mounted. Determining the type of the syringe body (112, 112', or 112") to which the smart flange (150) is mounted allows the smart flange (150) and/or a connected processor to determine the size of an injection from injection data corresponding to movement of the plunger member (described herein).

Figure 12A:
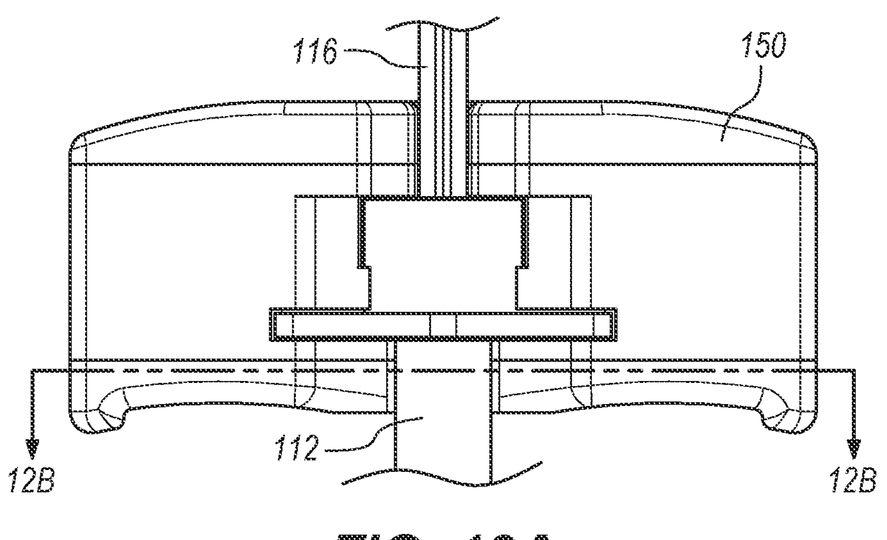
FIGS. 12A and 12B illustrates a smart flange with an injection sensor according to some embodiments.
Figure 12B:
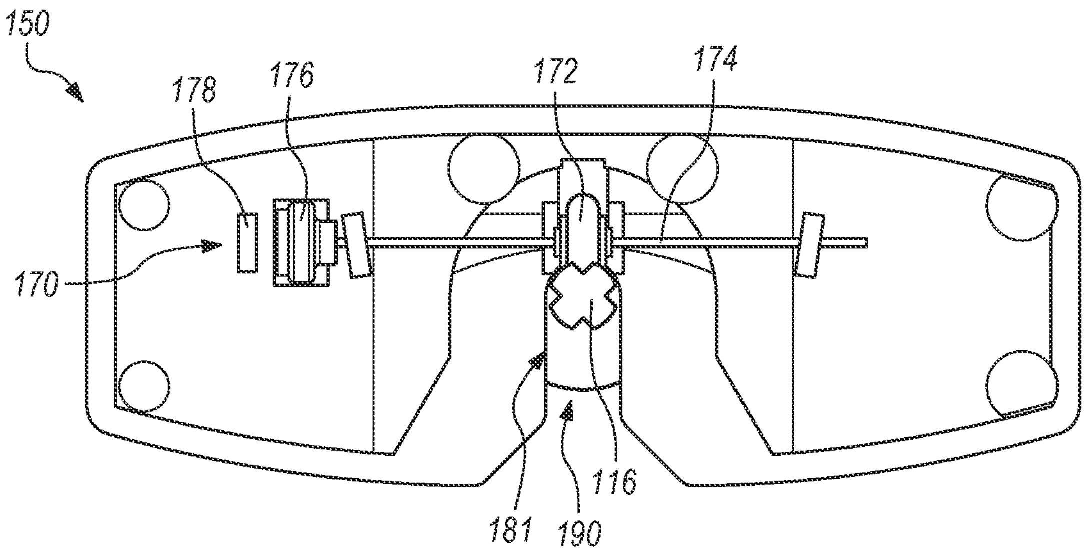

FIG. 12A depicts the level of the cross-sectional view of FIG. 12B in the smart flange (150). FIGS. 12A and 12B show a smart flange (150), according to some embodiments, mounted to a syringe body (112) with a plunger member (116 is) disposed therein. The smart flange (150) has an injection sensor (170) disposed therein. The injection sensor (170) is configured to measure injection data corresponding to the occurrence of an injection event (e.g., injection of a certain volume from an interior of the syringe body). The injection sensor (170) includes a wheel (172), which extends partially into the mounting opening/notch (190) defined by the smart flange (150). The injection sensor (170) also includes an injection elongate member (174) to which the wheel (172) is coupled. The injection elongate member (174) may be a metal wire or rod configured to elastically press the wheel (172) against the plunger member (116), such that axial movements of plunger member (116) rotate the wheel (172). The injection elongate member (174) is coupled to the wheel such that it rotates with the wheel (172). The injection sensor (170) further includes an injection magnetic member (176) coupled to a distal end of the injection elongate member (174), such that rotation of the injection elongate member (174) also rotates the injection magnetic member (176). Moreover, the injection sensor (170) includes a magnetic sensor (178) disposed adjacent the injection magnetic member (176) and configured to detect rotation of the injection magnetic member (176). The magnetic sensor (178) may be a magnetoresistive rotary sensor and/or may be a tunneling magneto resistance (TMR) sensor.

The injection magnetic sensor (178) generates injection data corresponding to rotation of the injection magnetic member (176). The smart flange (150) includes a processor to analyze the injection data to determine the direction and a magnitude of movement of the plunger member (116) relative to the smart flange (150). Determining the direction and magnitude of movement of the plunger member (116) allows the smart flange (150) and/or a connected processor to determine the occurrence of an injection event (i.e., withdrawal into and/or ejection out of the syringe body (112) of an amount of fluid). As described above, mounting data corresponding to a size of the syringe body (112) may also be used in determination of the amount of fluid withdrawn into and/or ejected out of the syringe body (112).

The mounting opening/notch (190) may be size and shape to allow a plunger member (116) with an X-shaped cross-section to enter the mounting opening/notch (190) only when it is rotated such that two of the four radially extending portions ("arms") of the X-shaped cross-section are in contact with the wheel (172). The smart flange (150) also includes a pair of orientation ribs (181; see FIGS. 8 and 12B) configured to limit the size and shape of the mounting opening/notch (190) such that the mounting opening/notch (190) orients or rotates the plunger member (116) such that two of the four arms of the X-shaped cross-section are in contact with the wheel (172). Such a configuration increases contact between the plunger member (116) and the wheel (172) when the wheel (172) is pressed against the plunger member (116) by the injection elongate member (174), thereby improving correspondence between axial movement of the plunger member (116) and rotation of the wheel (172).

In some embodiments, the injection sensor (170) can also function as a mounting sensor. In such embodiments, the plunger member (116) increases in size as the syringe body (112) increases in size. The sensor (170) with detect the increase in plunger member size using a mechanism similar to that described herein for mounting sensor (160).

Figure 13:
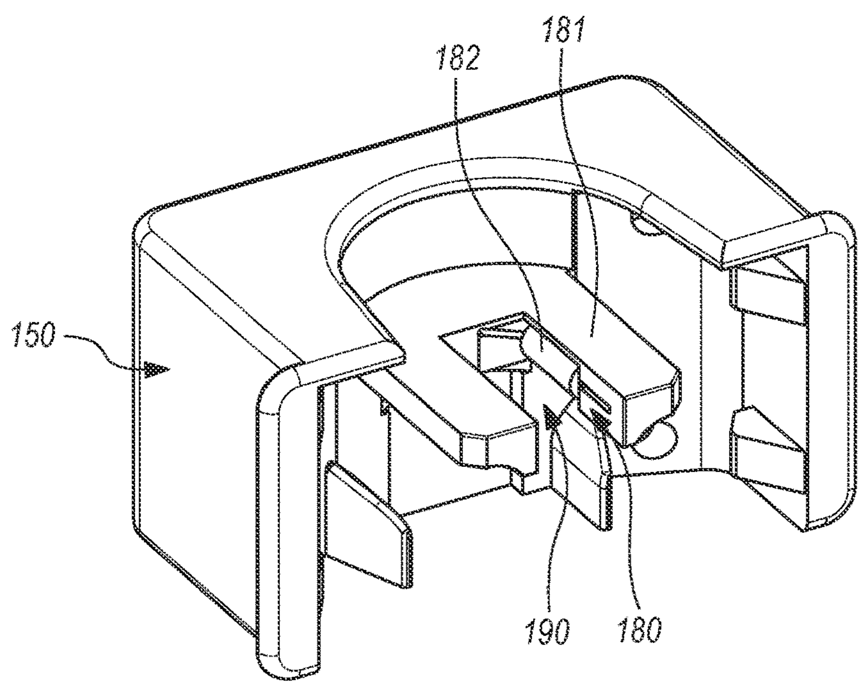
FIGS. 13 and 14 illustrate a smart flange with an injection sensor according to some embodiments.
Figure 14:
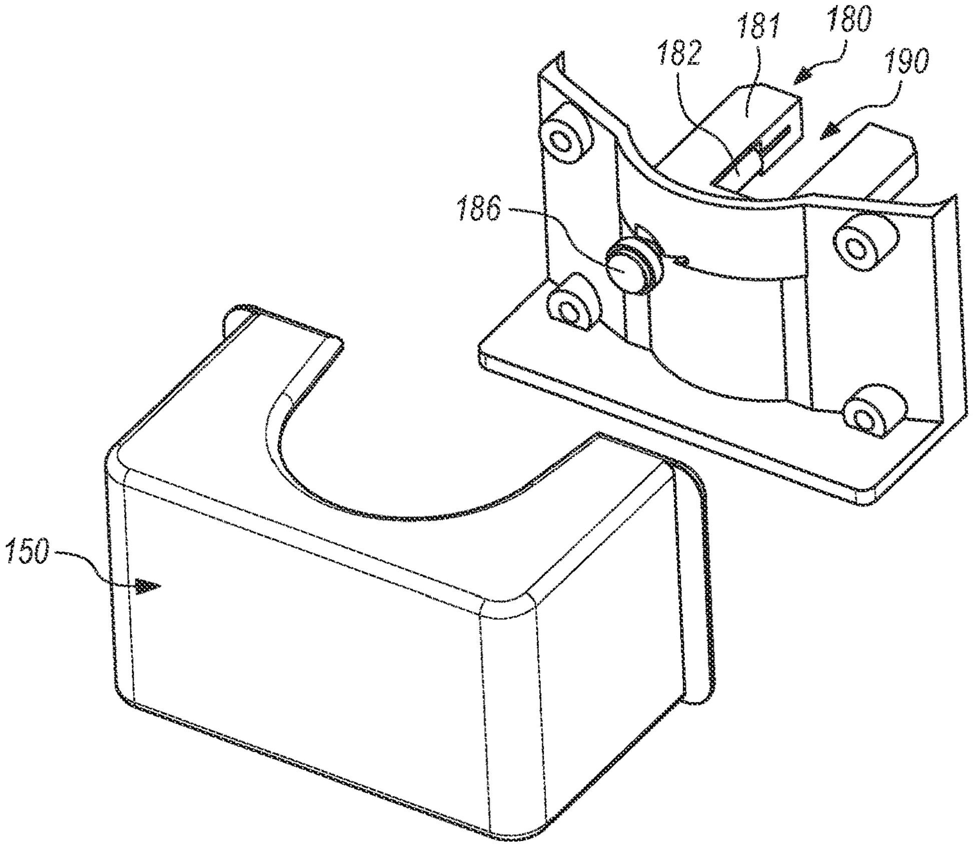
Figure 15:
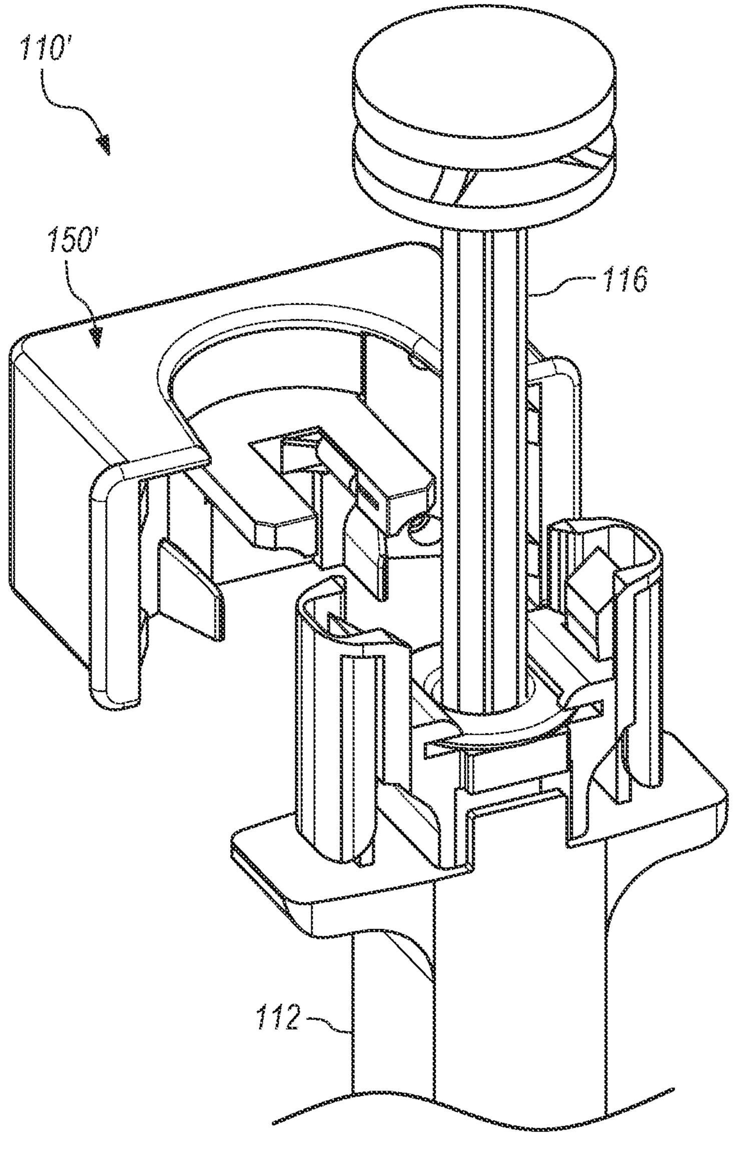
FIGS. 15 and 16 illustrate a smart flange with an injection sensor about to be and removably mounted on a syringe according to some embodiments.
Figure 16:
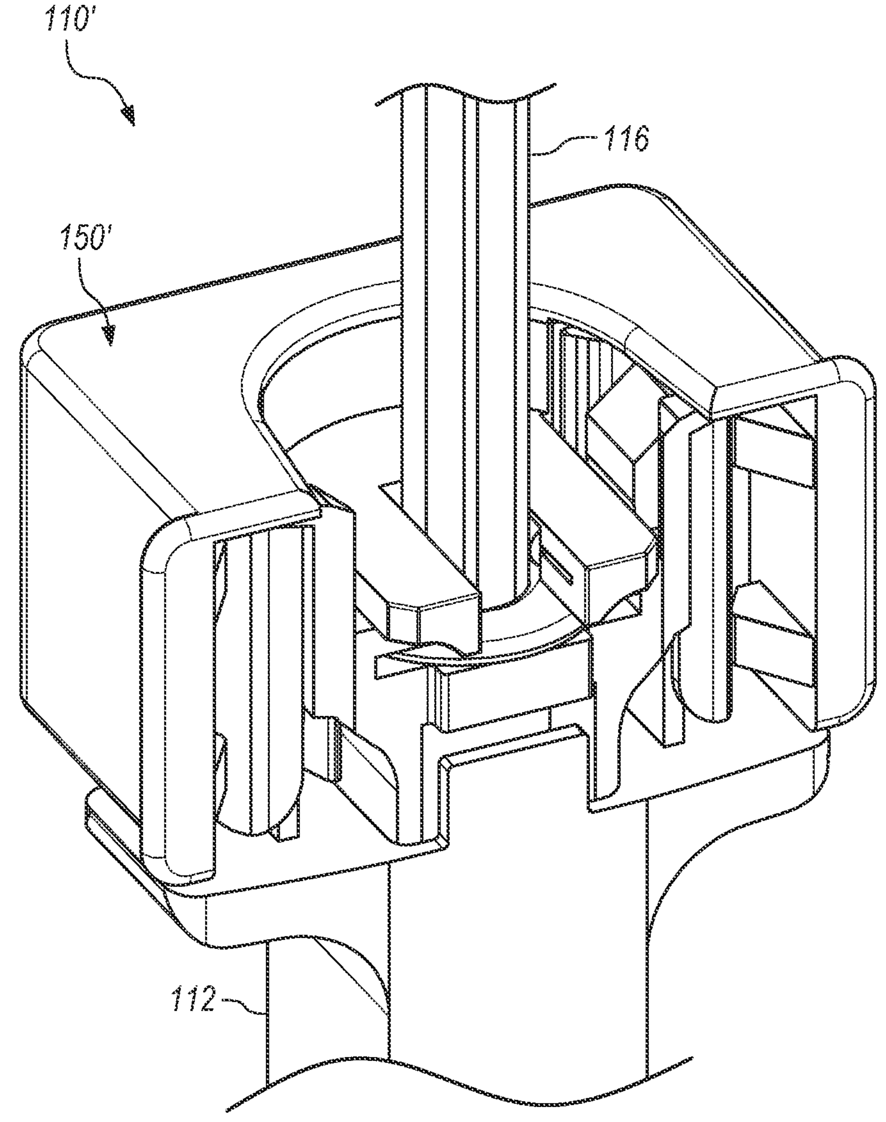

FIGS. 13 and 14 depict a smart flange (150'), according to some embodiments. FIGS. 15 and 16 depict the smart flange (150') about to be mounted onto a syringe body (112) with a plunger member (116) disposed therein. The smart flange (150') has an injection sensor (180) disposed therein. The injection sensor (180) is configured to measure injection data corresponding to the occurrence of an injection event (e.g., injection of a certain volume from an interior of the syringe body). The injection sensor (180) includes a roller (182), which is suspended in the smart flange (150') such that it extends partially into the mounting opening/notch (190) defined by the smart flange (150'). The injection sensor (180) also includes an injection magnetic member (186) coupled to a distal end of the roller (182), such that rotation of the injection elongate member (184) also rotates the injection magnetic member (186). Moreover, the injection sensor (180) includes a magnetic sensor disposed adjacent the injection magnetic member (186) and configured to detect rotation of the injection magnetic member (186). The magnetic sensor may be a magnetoresistive rotary sensor.

The injection magnetic sensor generates injection data corresponding to rotation of the injection magnetic member (186). The smart flange (150') includes a processor to analyze the injection data to determine the direction and a magnitude of movement of the plunger member (116) relative to the smart flange (150'). Determining the direction and magnitude of movement of the plunger member (116) allows the smart flange (150') and/or a connected processor to determine the occurrence of an injection event (i.e., withdrawal into and/or ejection out of the syringe body (112) of an amount of fluid). As described above, mounting data corresponding to a size of the syringe body (112) may also be used in determination of the amount of fluid withdrawn into and/or ejected out of the syringe body (112).

The smart flange (150') includes a pair of orientation ribs (181) configured to limit the size and shape of the mounting opening/notch (190) such that the mounting opening/notch (190) orients or rotates a plunger member (116) with an X-shaped cross-section as it enters the mounting opening/notch (190) such that two of the four radially extending portions ("arms") of the X-shaped cross-section are in contact with the roller (182). Such a configuration increases contact between the plunger member (116) and the roller (182) when the roller (182) is pressed against the plunger member (116) by its suspension mechanism, and when the plunger member (116) is either prevented from moving away from the roller (182) by another orientation rib that either includes an opposite facing roller (pressing against the plunger member from the opposite direction) or does not include a roller, thereby improving correspondence between axial movement of the plunger member (116) and rotation of the roller (182).

While the injection sensors (170, 180) are described as a magnetic sensor, in other embodiments, injection sensors may utilize other measurement modalities. In some embodiments, injection sensors are optical sensors that measure rotation of various light and dark areas rotatably coupled to a wheel. In some embodiments, injection sensors are capacitive sensors (see below).

Figure 17:
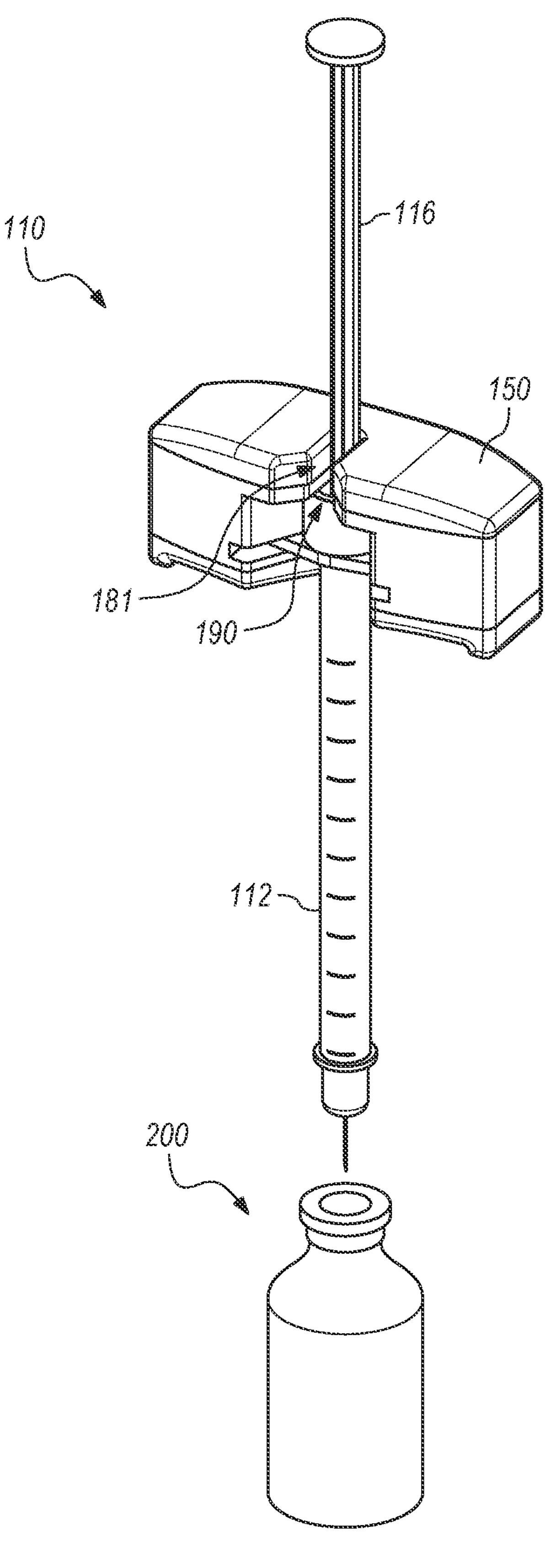
FIGS. 17 to 21 illustrate a method of injecting a medicine from a vial using a syringe with a smart flange removably coupled thereto according to one embodiment.

FIGS. 17 to 21 depict an injection system (110) including a smart flange (150) according to some embodiments used in the injection of a liquid medicine (e.g., insulin). The smart flange (150) includes a pair of orientation ribs (181) configured to limit the size and shape of a mounting opening/notch (190) that orients or rotates a plunger member (116) with an X-shaped cross-section as it enters the mounting opening/notch (190) such that two of the four radially extending portions ("arms") of the X-shaped cross-section are facing inward in the mounting opening/notch (190) in contact with a sensor. FIG. 17 depicts the injection system (110) before the liquid medicine is taken up into the syringe body (112). The smart flange (150) has already been mounted onto the syringe body (112). In some embodiments, mounting the smart flange (150) on to the syringe body (112) activates the processors in the smart flange (150). A mounting sensor in the smart flange (150) can detect the presence and type (e.g., size) of the syringe body (112) as described herein.

Figure 18:
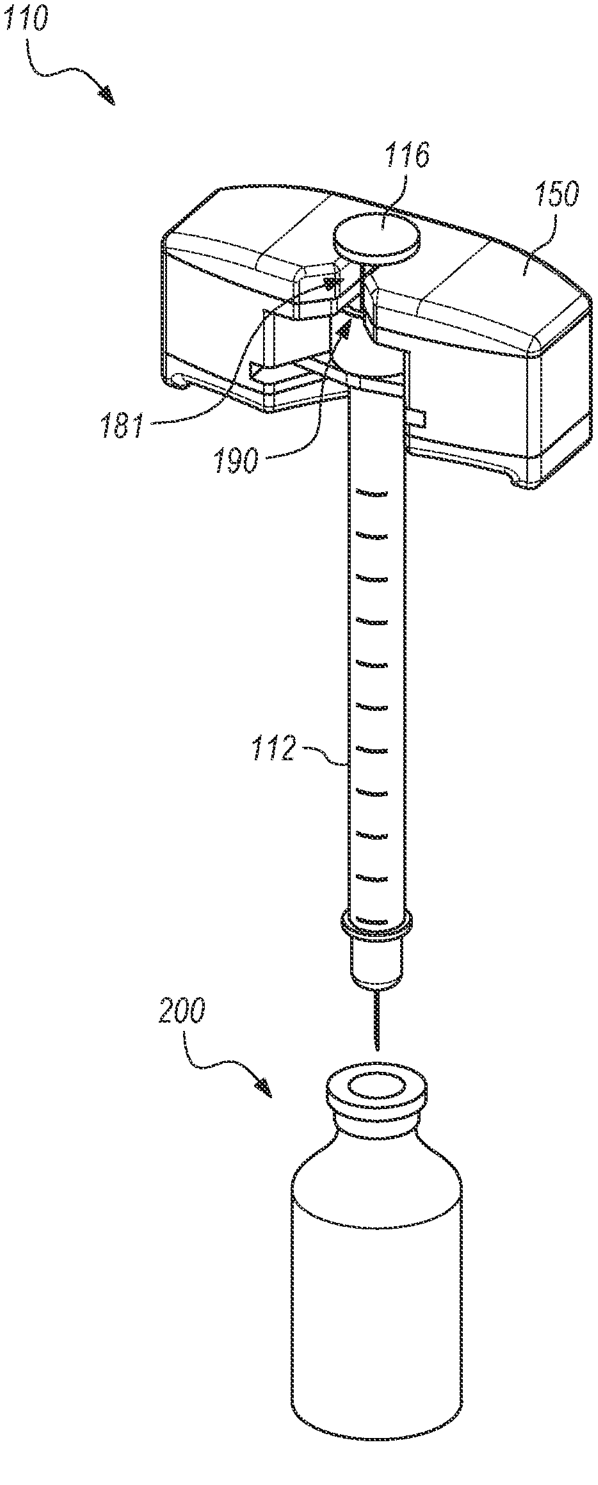

FIG. 18 depicts the penetration of a vial (200) of liquid medicine by the injection system (110) and injection of air into the vial (200). An injection sensor in the smart flange (150) can measure movement of the plunger member (116) and determine the volume of air injected into the vial (200).

Figure 19:
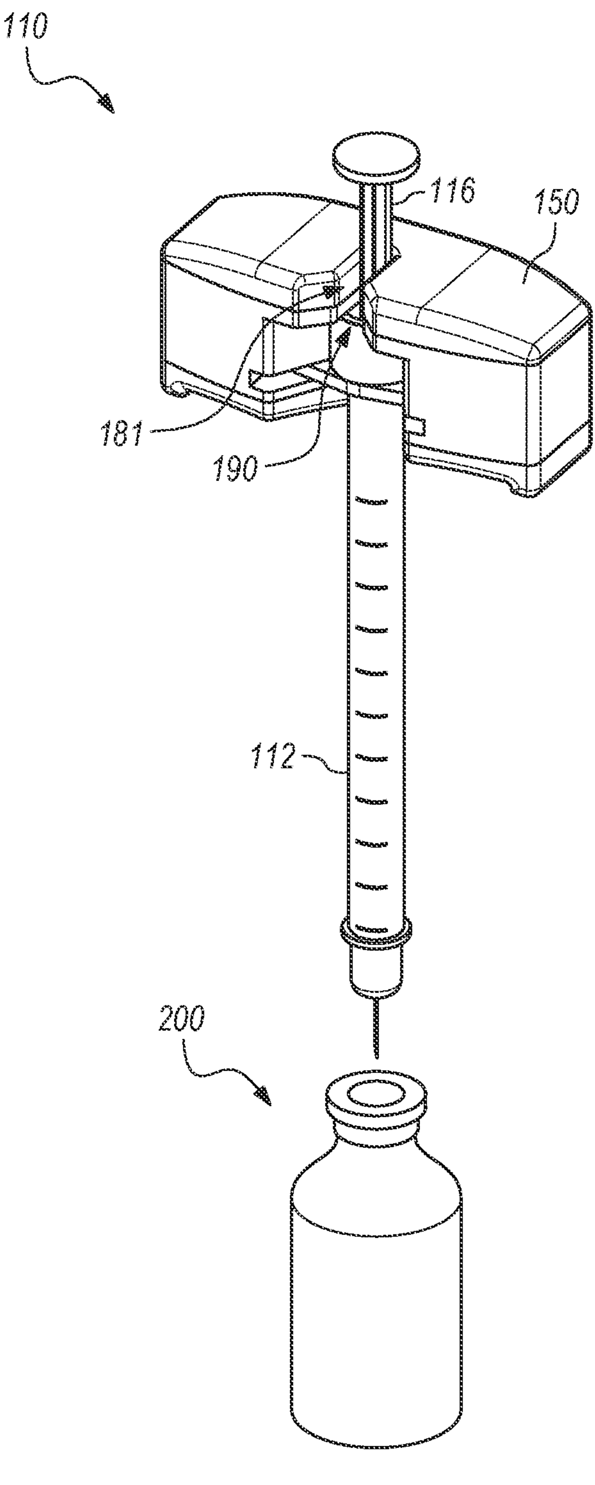

FIG. 19 depicts some air being forced by increased pressure in the vial (200) back into the syringe body (112). The injection sensor in the smart flange (150) can measure movement of the plunger member (116) and determine the volume of air pushed back into the syringe body (112).

Figure 20:
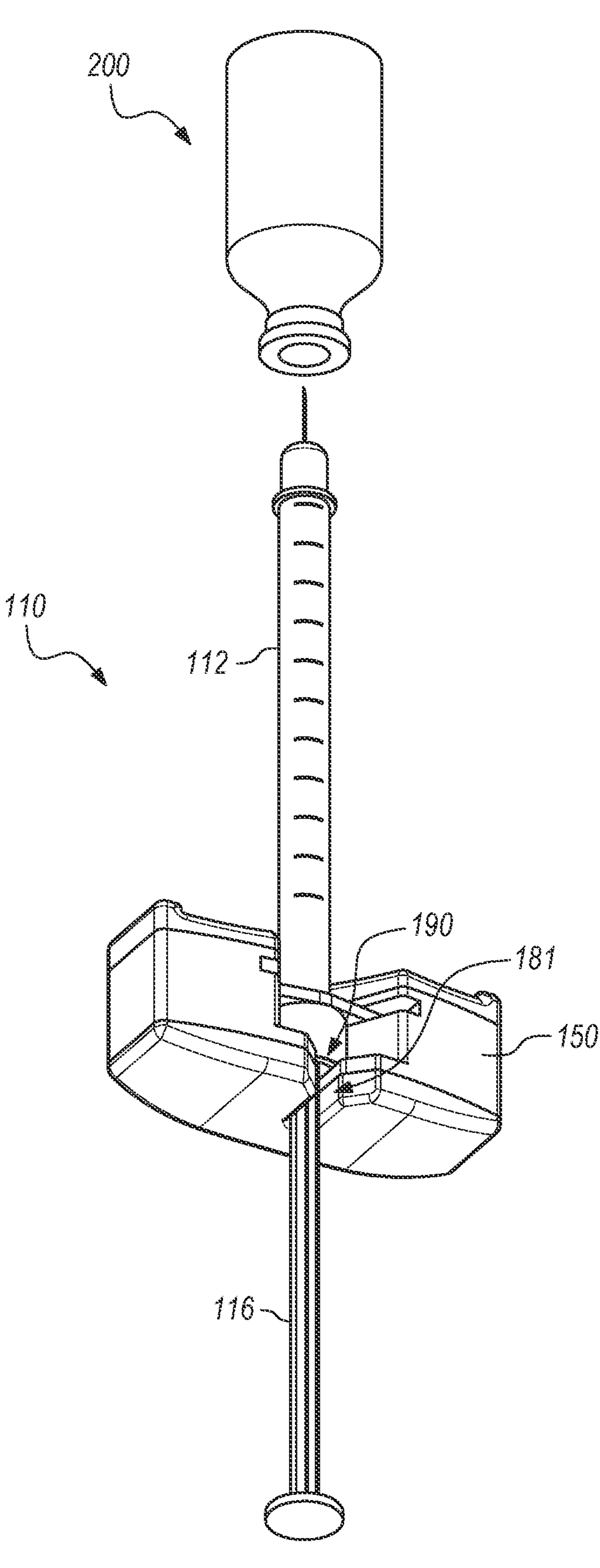

FIG. 20 depicts withdrawal of some of the liquid medicine from the vial (200) into the syringe body (112) after in version of the injection system (110) and the final (200) attached thereto. The injection sensor in the smart flange (150) can measure movement of the plunger member (116) and determine the volume of liquid medicine withdrawn into the syringe body (112). The smart flange (150) may also include an orientation sensor, such as an accelerometer, tip sensor, gyroscope, or other inertial motion unit sensor, to confirm that the injection system (110) is inverted or oriented with the vial seal facing downward when inserted into the vial during withdrawal of the liquid medicine. An alternative embodiment for the injection system (110) provides a button for the user to press once the appropriate amount of insulin in drawn up to tell the smart flange (150) that the syringe (112) is filled and ready for injection. The button may be located on the proximal or distal surfaces of the smart flange (150).

Figure 21:
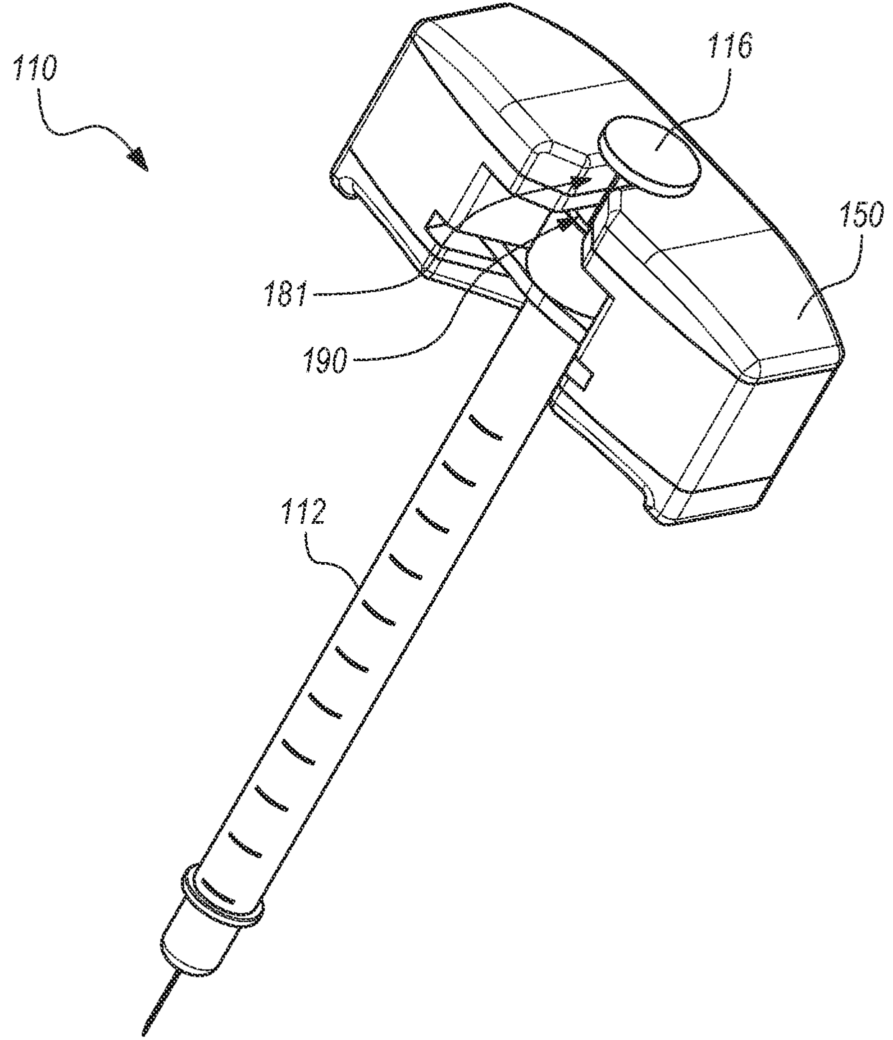

FIG. 21 depicts the injection system (110) after injection of the liquid medicine into a patient. The injection sensor in the smart flange (150) can measure movement of the plunger member (116) and determine the volume of liquid medicine ejected from the syringe body (112).

All of the data collected during the injection steps depicted in FIGS. 17 to 21 can be recorded in the smart flange (150) and/or transmitted to a processor of a medical treatment management system. Collection, analysis, and storage of the mounting and injection related data described herein can more accurately monitor injections, thereby improving medical treatments. Further details regarding smart flanges and other injection collection systems and methods are described in U.S. patent application Ser. Nos. 15/985,354 and 17/169,806, the contents of which have been previously Incorporated by reference herein.

Figure 22:
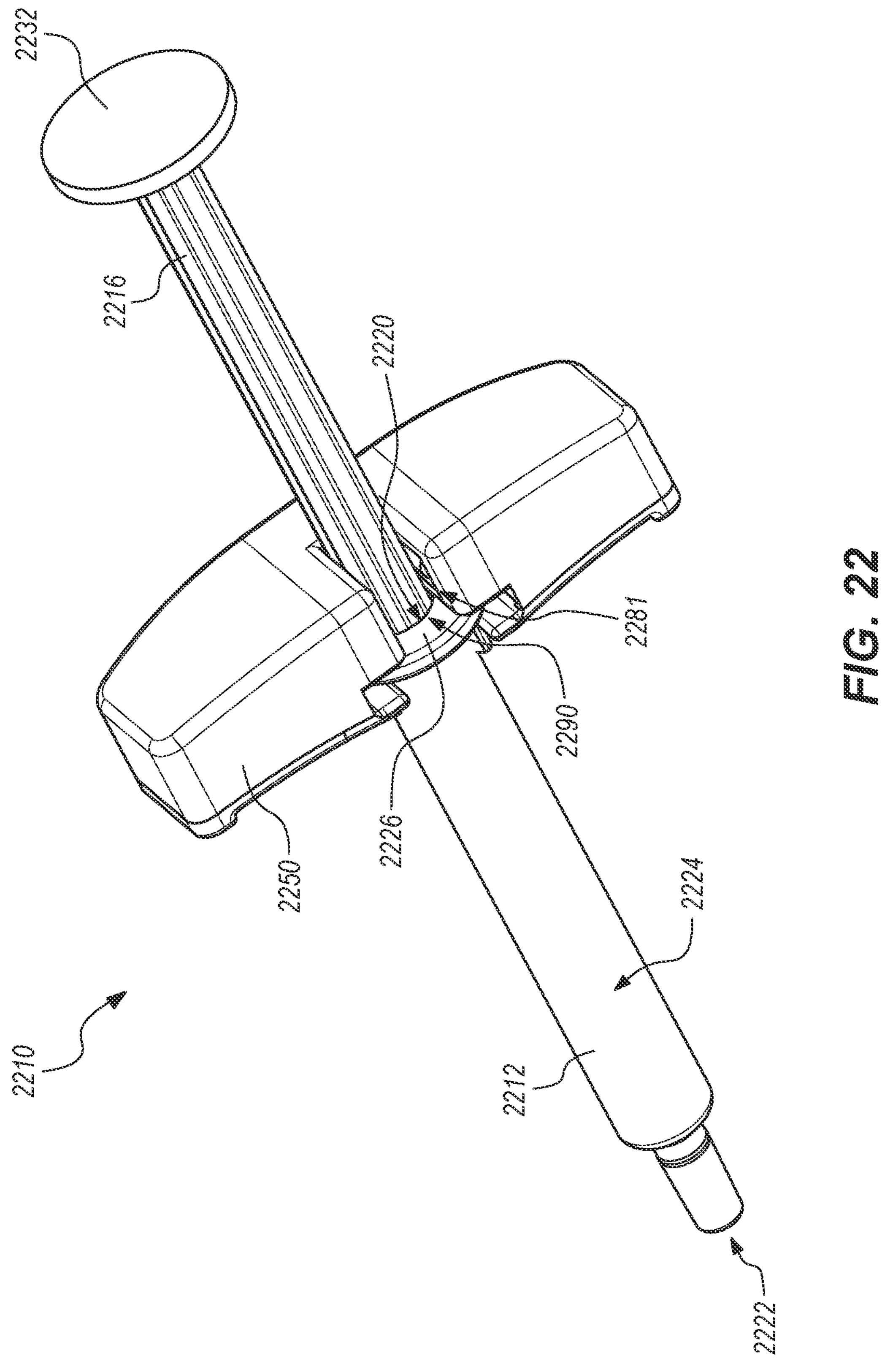
FIG. 22 illustrates a smart flange removably coupled to a syringe according to some embodiments.

FIG. 22 depicts an injection system (2210) according to some embodiments. The injection system (2210) also includes a syringe body (2212), a stopper member (not shown, see the stopper member (114) in FIG. 6), a plunger member (2216), and a smart flange (2250) removably attached to the syringe body (2212). The syringe body (2212) includes an open proximal end (2220) and an open distal end (2222). The open distal end (2222) may be coupled to a needle assembly (not shown) The syringe body (2212) also includes a syringe interior (2224), a syringe flange (2226) at the proximal end (2220) thereof. Similar to the injection system (110) depicted in FIG. 6, the plunger member (2216) may be manipulated to insert the stopper member (not shown) distally into the syringe interior (2224) to expel an injectable substance (e.g., fluid) from the syringe interior (2224) through the open distal end (2222). The plunger member (2216) includes a proximal end pad (2232) to facilitate manual manipulation of the plunger member (2216) using a digit (e.g., a thumb) of a user's hand while one or more other digits of the user's hand provide an opposing force (e.g., against a distal side of the syringe flange (2226) or a smart flange (2250) disposed thereon).

Figure 23A:
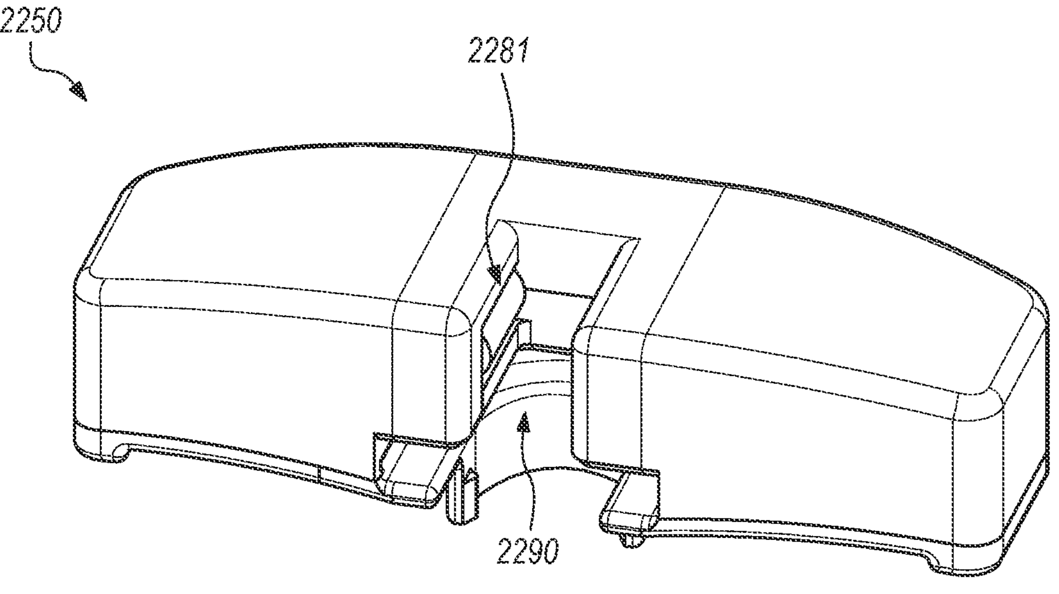
FIGS. 23A and 23B illustrate a smart flange before it is removably coupled to a syringe according to some embodiments.
Figure 23B:
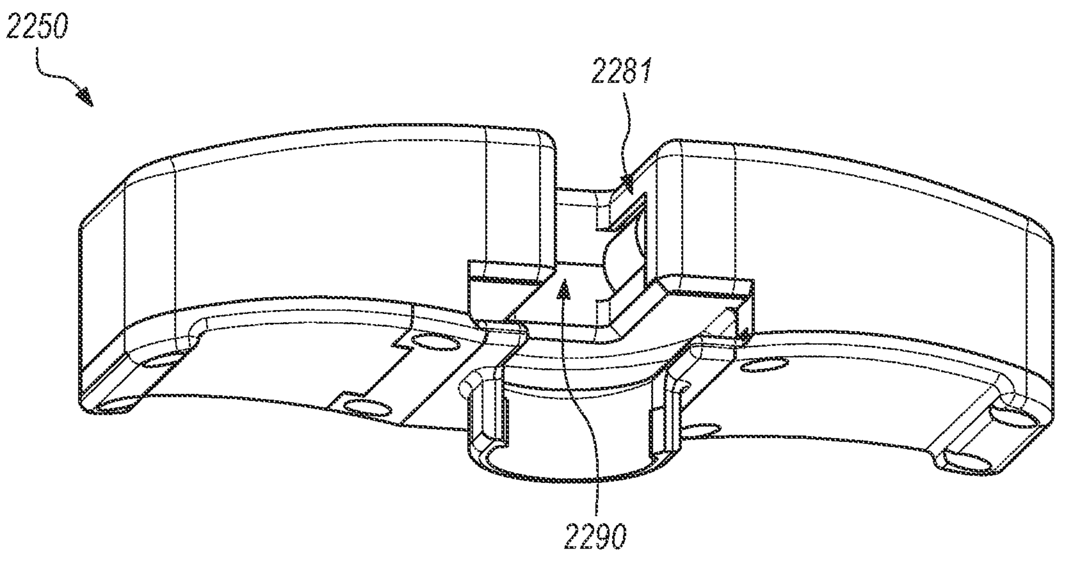
Figure 24:
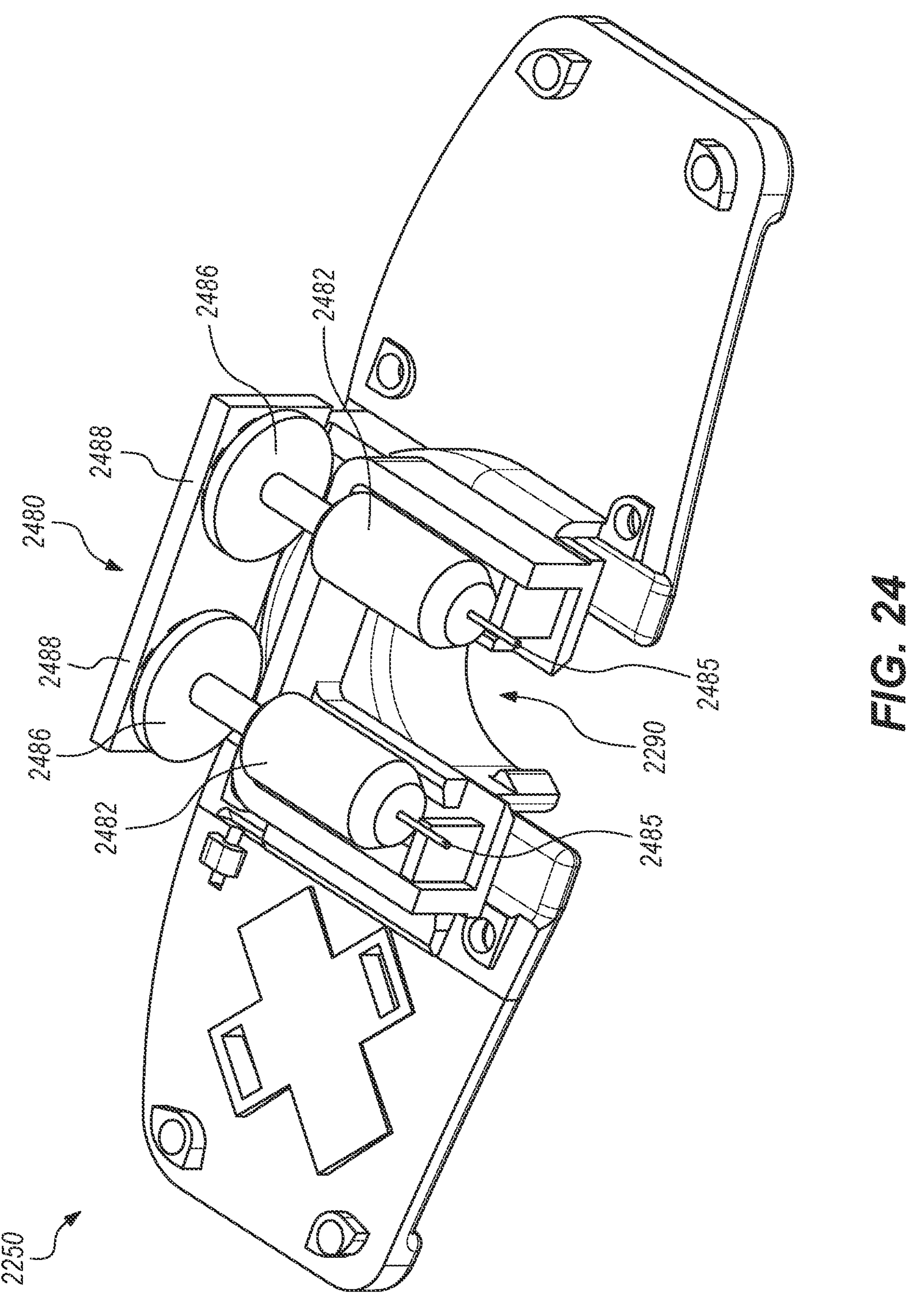
FIGS. 24 to 27 illustrate an injection sensor of a smart flange, with the smart flange housing and some components omitted for clarity, according to some embodiments.
Figure 25:
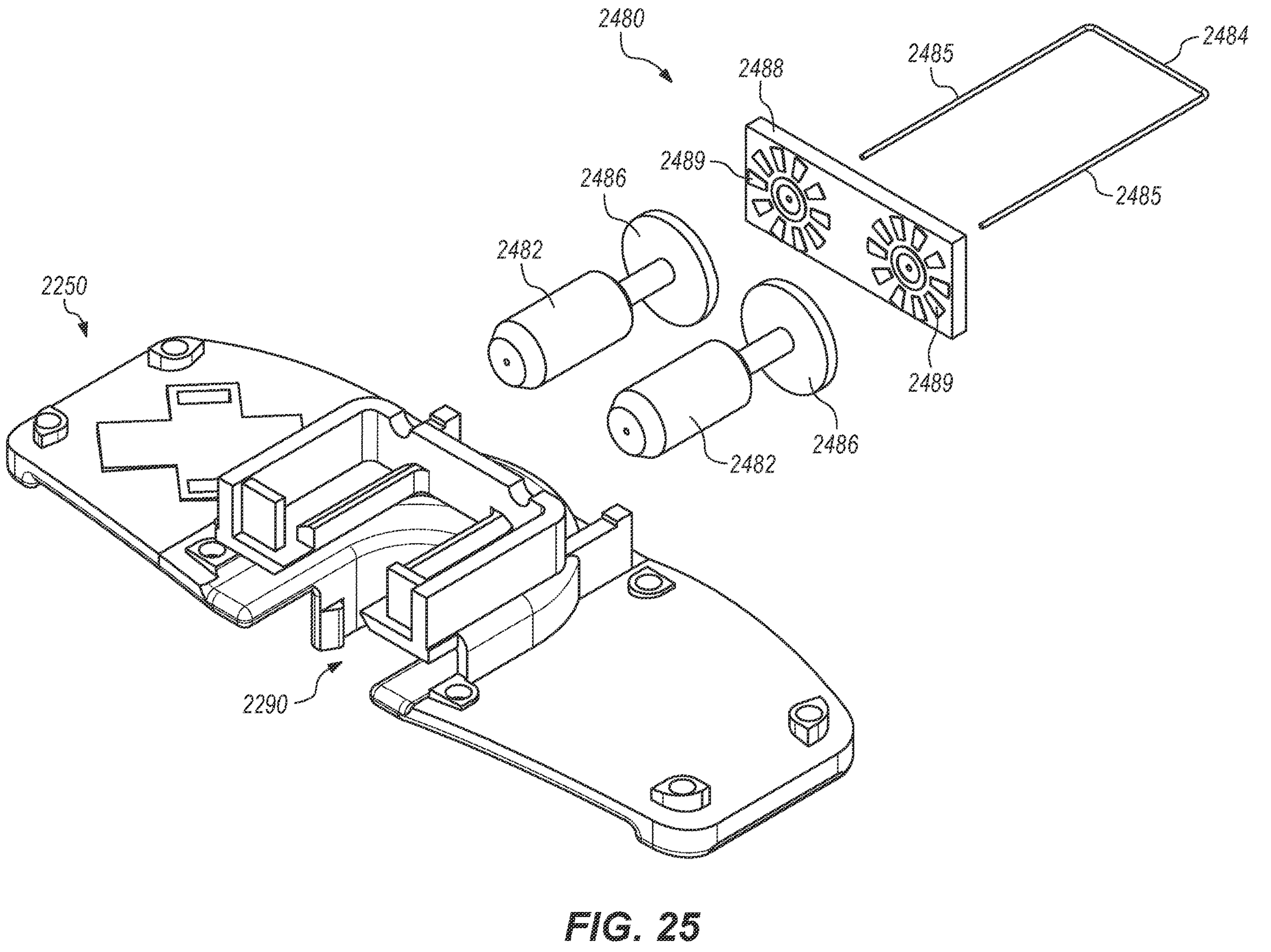
Figure 26:
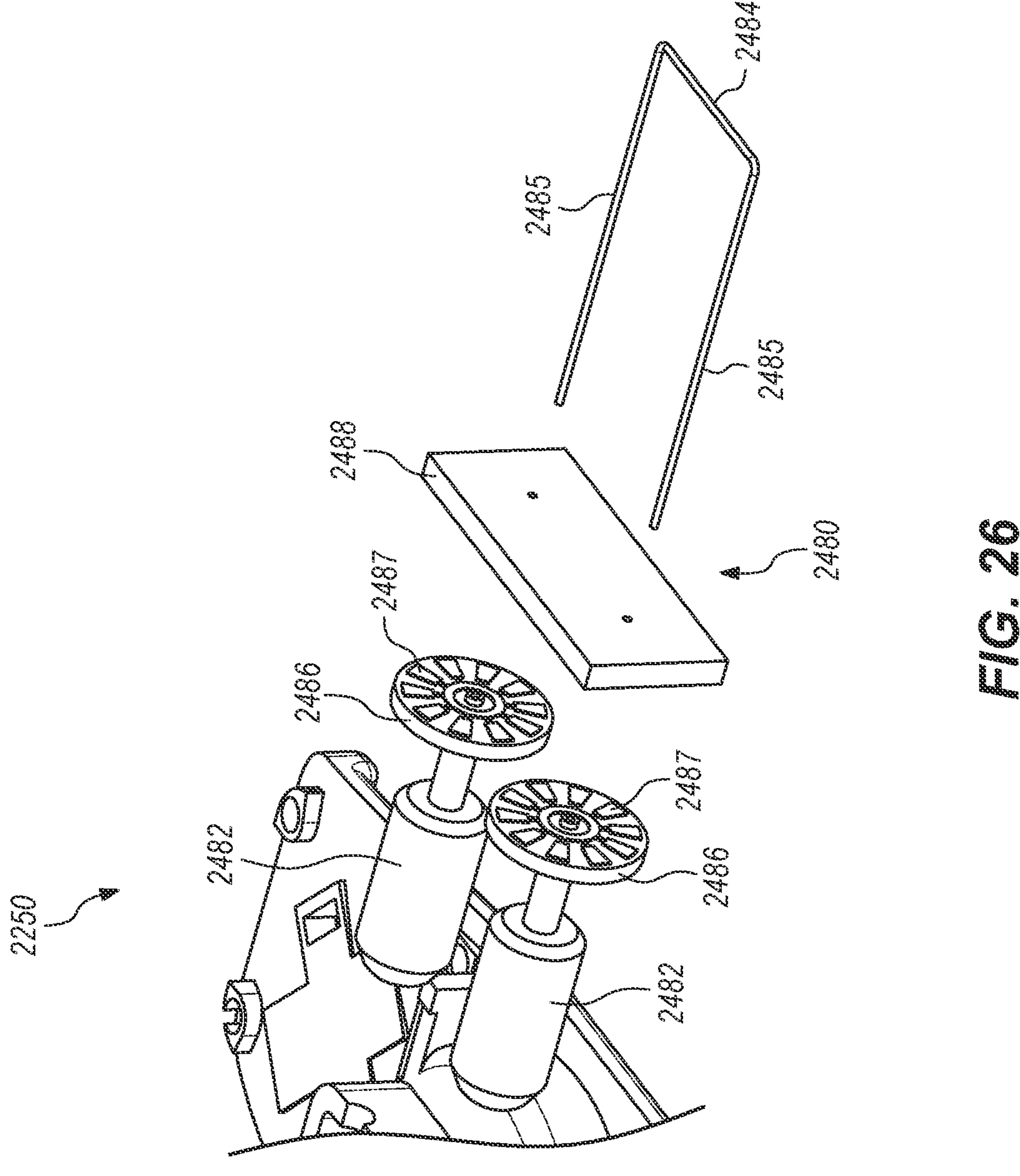
Figure 27:
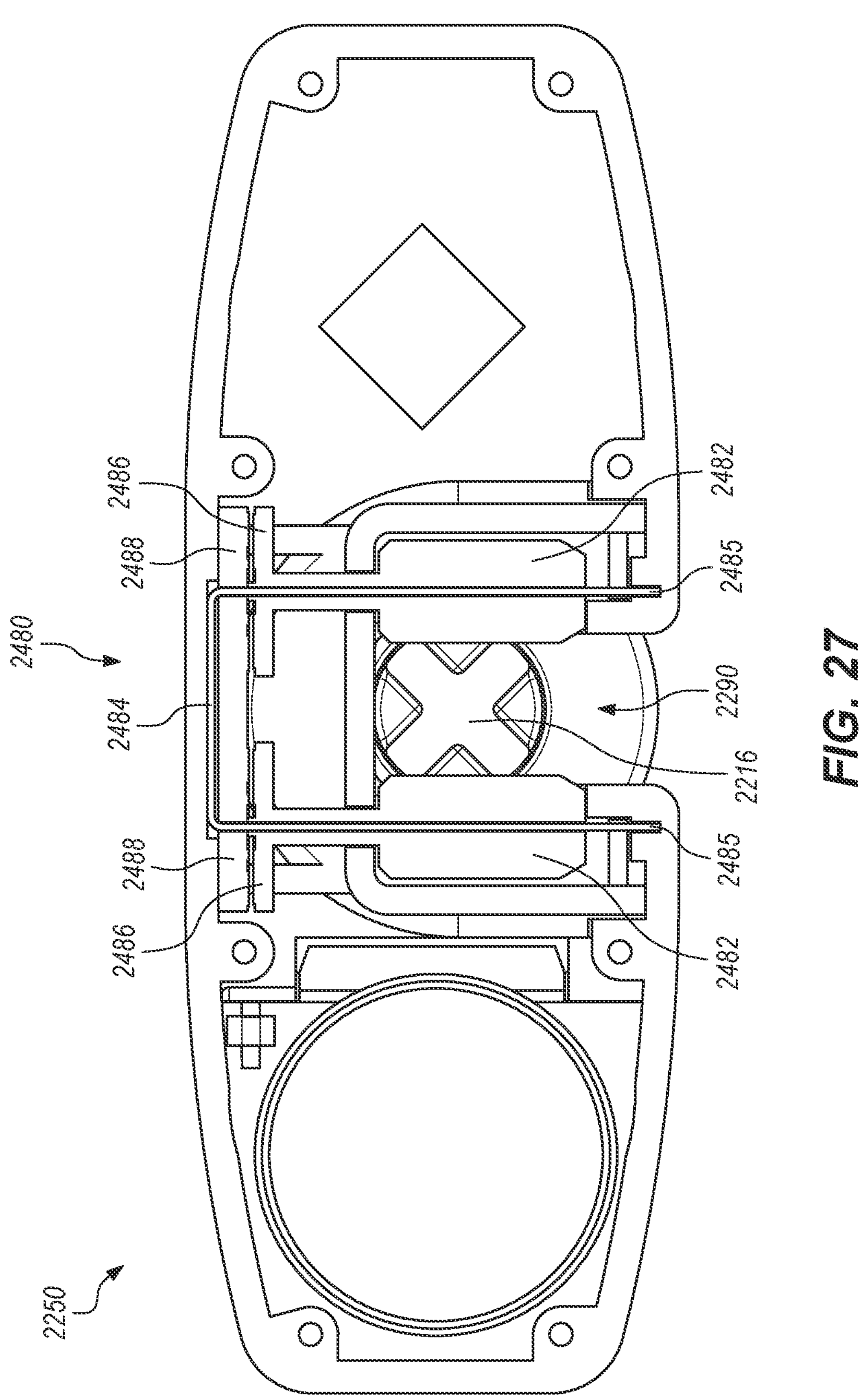

FIGS. 23A to 27 depict a smart flange (2250), according to some embodiments. FIGS. 23A, 23B, and 24 are perspective views. FIGS. 25 and 26 are exploded views. FIG. 27 is a cross-sectional view. In FIGS. 24 to 26, the housing and some components of smart flange (2250) are omitted for clarity The smart flange (2250) has an injection sensor (2480; see FIGS. 24 to 27) disposed therein. The injection sensor (2480) is configured to measure injection data corresponding to the occurrence of an injection event (e.g., injection of a certain volume from an interior of the syringe body and/or withdrawal of a certain volume from a vial into an interior of the syringe body). The injection sensor (2480) includes a pair of rollers (2482), which are suspended in the smart flange (2250) such that they extend partially into an mounting opening/notch (2290) defined by the smart flange (2250). Each of the rollers (2482) may include a mandrel covered by an elastic material (e.g., Robert). The injection sensor (2480) also includes a pair of rotor disks (2486) each coupled to a proximal end of respective rollers (2482), such that rotation of the rollers (2482) also rotates the rotor disks (2486). Moreover, the injection sensor (2480) includes a pair of capacitive sensors (2488; see FIG. 25) disposed adjacent respective rotor disks (2486) and configured to detect rotation of the respective rotor disks (2486). The smart flange (2250) includes a pair of orientation ribs (2281) configured to limit the size and shape of a mounting opening/notch (2290) such that the mounting opening/notch (2290) orients or rotates a plunger member (2216) with an X-shaped cross-section as it enters the mounting opening/notch (2290) such that opposite pairs of the four radially extending portions ("arms") of the X-shaped cross-section are in contact with a sensor each roller (2482).

As shown in FIG. 26, the rotor disks (2486) include a plurality of metal pads (2487) disposed around the rotor disks (2486). As shown in FIG. 25, the capacitive sensors (2488) include a stator (2489) formed of a plurality of metal pads on and integrated circuit board. Rotation of the rotor disks (2486) relative to respective stators (2489) generates a changing capacitance, which can be detected by the capacitive sensors (2488) using the air between the rotor disks (2486) and the stators (2489) as a dielectric. The capacitive sensors (2488) apply a high frequency signal (e.g., current) to the respective stators (2489) in order to detect the changing capacitance. The metal pads (2487) can be formed on the rotor disks (2486) and the stators (2488) using lithographic techniques.

Capacitive sensors such as those described herein require very little power and therefore facilitate low profile smart flanges. In some embodiments, a dielectric material can be applied between the rotors and stators. In some embodiments, a second pair of capacitive sensors can be disposed on the opposite side of the rotor disks from the first pair of capacitive sensors. In some embodiments, a sinusoidal pattern can be formed on the rotor disks and/or the stators instead of metal pads.

As shown in FIGS. 25 to 27, a U-shaped member (2484) is threaded through the capacitive sensors (2488), the stators (2489), the rotor disks (2486), and the rollers (2482) to physically couple these parts together while allowing the rollers (2482) to rotate on the U-shaped member (2484). The U-shaped member (2484) has a pair of arms (2485) that are biased toward each other, such that the rollers (2482) threaded onto the respective arms (2485) are biased toward each other across the mounting opening/notch (2290). As such, the rollers (2482) are configured to squeeze opposite sides of a plunger member (2216) to improve contact between the rollers (2482) and the plunger member (2216), as shown in FIG. 27. Improving contact between the rollers (2482) and the plunger member (2216) improves accuracy of plunger member (2216) movement detection by the injection sensor (2480). Further, having two rollers (2482) allows a processor to detect differential or absolute movement of the plunger member (2216). Having to rollers (2482) also allows the processor to utilize a maximum rotation/movement value in case one of the rollers (2482) skips during movement of the plunger member (2216). The U-shaped member (2484) is also movable along a long axis of the smart flange (2250) to provide the rollers (2482) with tolerance to accept various plunger members (2216).

The injection capacitive sensor (2488) generates injection data corresponding to rotation of the rotor disks (2486). The smart flange (2250) includes a processor to analyze the injection data to determine the direction and a magnitude of movement of the plunger member (2216) relative to the smart flange (2250). Determining the direction and magnitude of movement of the plunger member (2216) allows the smart flange (2250) and/or a connected processor to determine the occurrence of an injection event (i.e., withdrawal into and/or ejection out of the syringe body (2212) of an amount of fluid). As described above, mounting data corresponding to a size of the syringe body (2212) may also be used in determination of the amount of fluid withdrawn into and/or ejected out of the syringe body (2212).

In some embodiments, a mounting sensor may share components with the injection sensor (2480). For instance, a contact member may be coupled to the first and/or second rollers (2482). A contact detector may be disposed adjacent the contact member such that deforming the first and/or second rollers (2482) away from each other places the contact member in contact with the contact detector. Contact between the contract member and the contact detector may send a signal to a processor to indicate that the smart flange (2250) is mounted to a syringe (2212).

Figure 28:
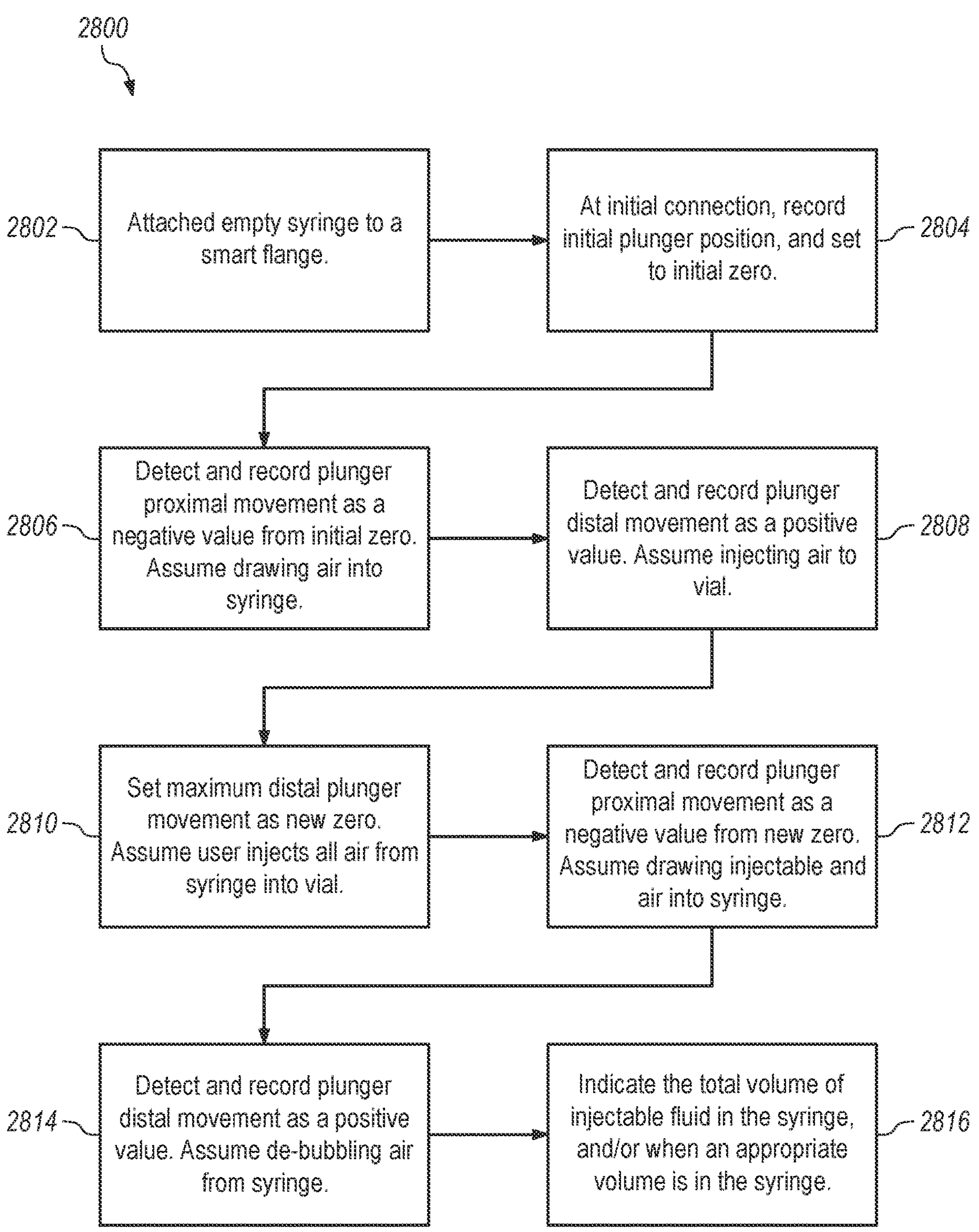
FIG. 28 is a flow chart illustrating a method of injecting a medicine from a vial while determining the amount of medicine injected using a syringe with a smart flange removably coupled thereto according to some embodiments.
Figure 29:
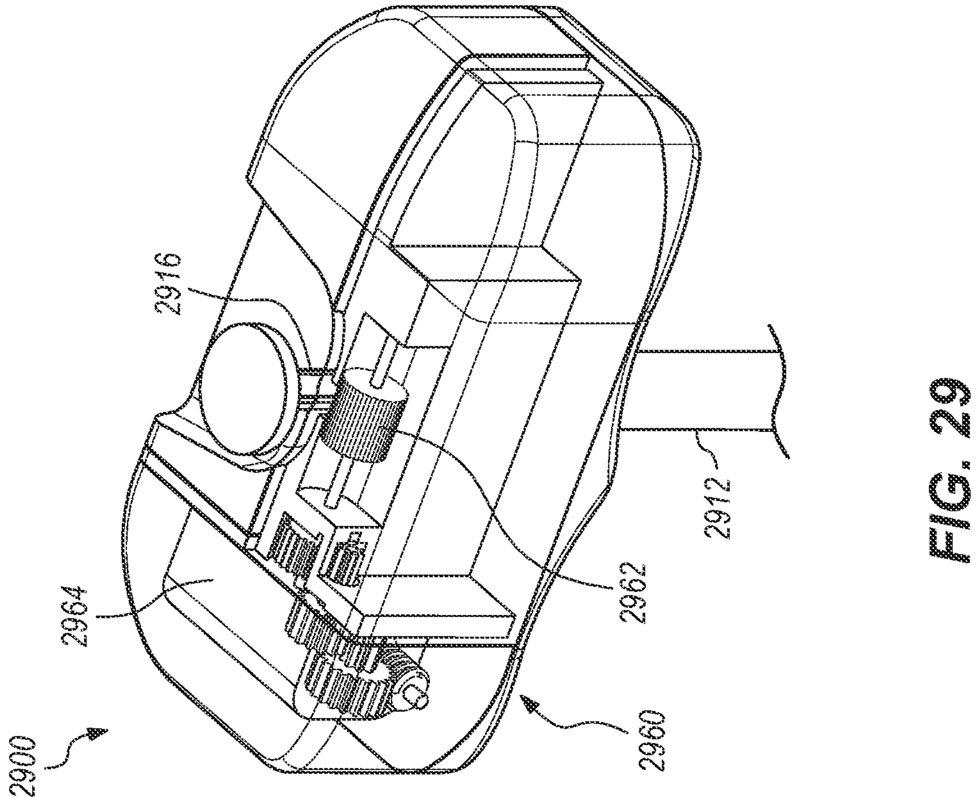
FIGS. 29 to 32 illustrate a smart flange removably coupled to a syringe and including a plunger driver according to some embodiments.
Figure 30:
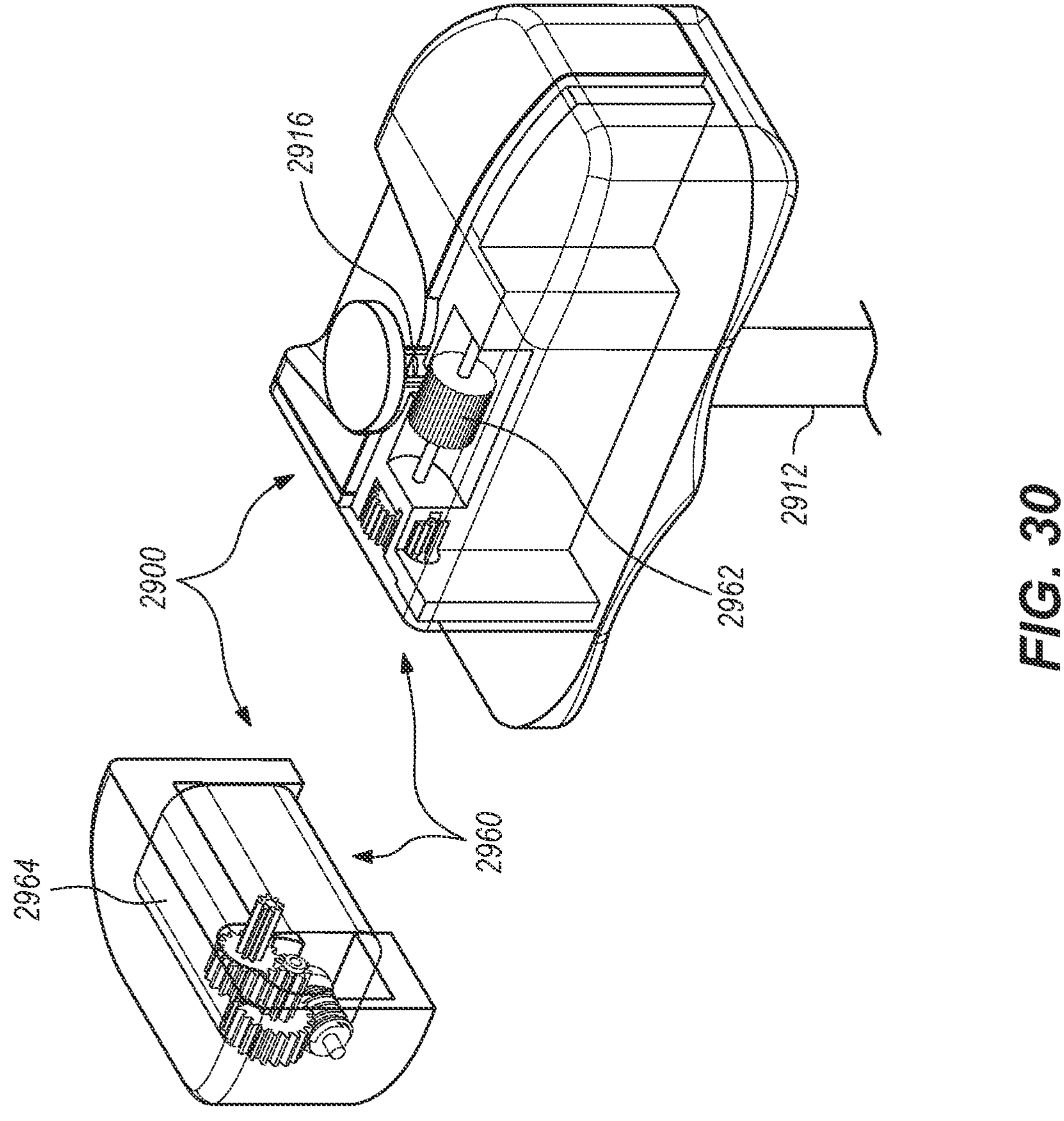

FIG. 28 is a flow chart depicting a method (2800) of injecting an injectable fluid (e.g. a liquid medicine) from a vial while determining the amount of fluid injected using a syringe with a smart flange (such as those described herein) removably coupled thereto according to some embodiments.

At step (2802), an empty syringe (e.g., an insulin syringe) is attached to a smart flange having a mounting sensor and an injection/position sensor. At step (2804), at the time of initial connection of the empty syringe to the smart flange, the smart flange records the initial plunger member position, and sets that initial plunger member position to an "initial zero".

At step (2806), the smart flange detects and records proximal movement of the plunger member as a negative value from initial zero. The smart flange may be programmed to assume that proximal movement of the plunger member after initial connection is a user drawing air into the syringe.

At step (2808), the smart flange detects and records distal movement of the plunger member as a positive value. The smart flange may be programmed to assume that distal movement of the plunger member after initial proximal movement is a user injecting air into a vial of injectable fluid (e.g., insulin) to avoid vapor lock. The smart flange may be programmed to assume that the distal maximum to which the plunger member moves corresponds to a member coupled to the plunger member reaching a distal end of the syringe.

At step (2810), the smart flange sets the distal maximum to which the plunger member moves as a "new zero" for distance/volume measurements later in the injection process. Accordingly, the smart flange is programmed to set the plunger member position at the bottom of the syringe as a "new zero" position.

At step (2812), the smart flange detects and records proximal movement of the plunger member as a negative value from new zero. The smart flange may be programmed to assume that proximal movement of the plunger member after setting the new zero is a user drawing injectable fluid (e.g., insulin) and air into the syringe.

At step (2814), the smart flange detects and records distal movement of the plunger member as a positive value. The smart flange may be programmed to assume that minor distal movement of the plunger member is a user expelling air drawn in with the injectable fluid. Some embodiments, a position sensor may be used to detect substantially upward positioning of the distal end of the syringe during this purging/de-bubbling process.

At step (2816), the smart flange calculates and records the amount of injectable fluid in the syringe after air is expelled from the syringe in step (2814). In some embodiments, the value of injectable fluid in the syringe may be displayed on a smartphone wirelessly coupled to the smart flange and/or announced via a speaker on a smartphone or the smart flange. A green light or an audio indicator may also be presented to indicate when a predetermined appropriate volume of the injectable fluid has been drawn up into the syringe.

In some embodiments, the display of the volume of injectable fluid in the syringe may be indicated with large digits for visually impaired users. In some embodiments, the real-time volume of injectable fluid in the syringe (e.g., after de-bubbling) may be audibly announced (e.g., "10U," "20U," "30U," etc.) to facilitate use by visually impaired users. In some embodiments, the smart flange may issue a visual and/or audible warning when an inappropriate amount of injectable fluid (e.g., an overly large dose of insulin) has been drawn up into the syringe.

FIGS. 29 to 32 illustrates a smart flange (2900) removably coupled to a syringe body (2912) and including a plunger driver (2960) according to some embodiments. The plunger driver (2960) is configured to move a plunger member (2916) along a longitudinal axis thereof. The plunger driver (2960) includes a drive wheel (2962), a motor (2964) to rotate the drive wheel (2962), and an idler wheel (2966) to urge the plunger member (2916) against the drive wheel (2962).

Figure 31:
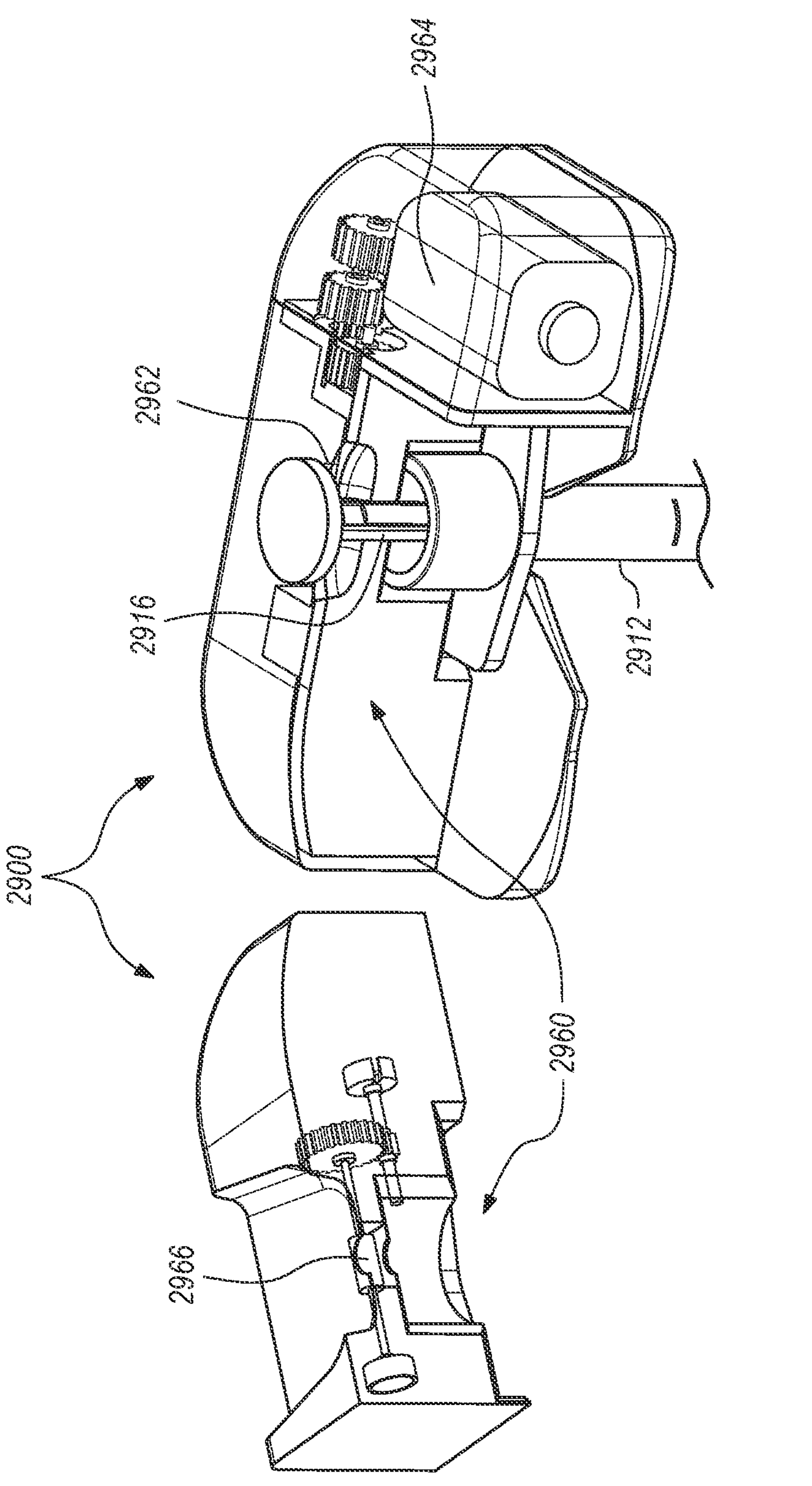
Figure 32:
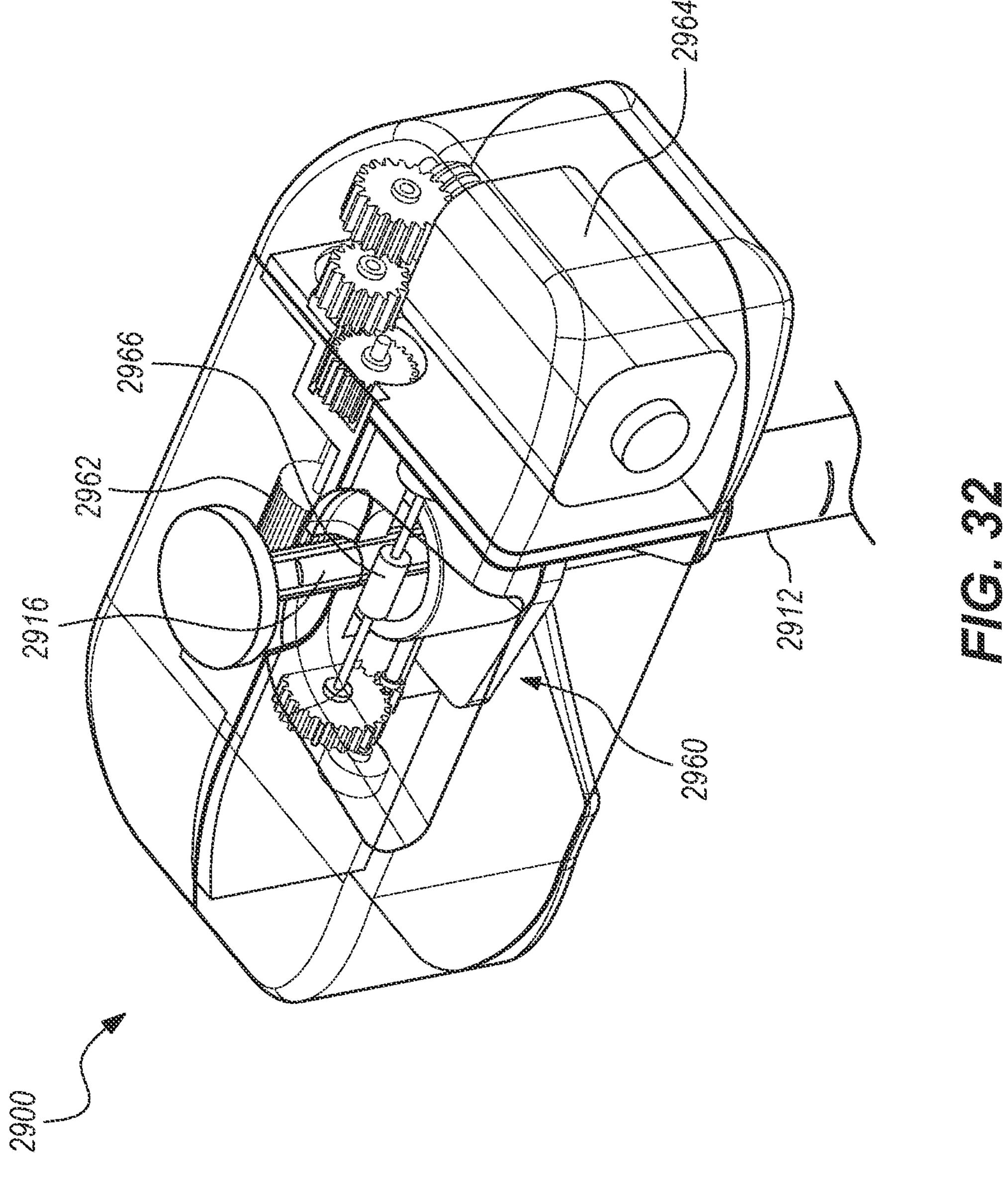

The drive wheel (2962) may be a new knurled rubber and/or metal wheel are configured to advance and retract the plunger member (2916). The motor (2964) may be an off-the-shelf DC motor with a custom gearbox to increase torque. The idler wheel (2966) may be spring-loaded to squeeze the plunger member (2916) against the drive wheel (2962). As shown in FIG. 31, the smart flange (2900) may have a clamshell design for engaging the idler wheel (2966) against the plunger member (2916).

The plunger driver (2960) in the smart flange (2900) facilitates use of the injection system (2900) for visually impaired and/or dexterity impaired users. Especially when combined with an injection sensor such as those described herein, a smart flange (2900) with the plunger driver (2960) can automate injection of fluid medicines by a user. For instance, such a smart flange (2900) can deliver a specific amount of insulin to diabetic patients depending on various other patient information such as glucose readings, food ingestion, exercise, etc. When the specific amount of insulin is driven by software from an application (coupled to a smart flange) versus driven by a user, this is a small step to creating a closed loop system such as an artificial pancreas.

Electronic Insulin Diary System with Smart Flange

The smart flange devices described herein contain electronic communication capabilities for receiving and/or transmitting information to/from a computing device. The computing device may be a mobile phone, smartphone, tablet, smart watch, personal computer, or other computing device. The combination of the smart flange device with a syringe and software running on the computing device allows for the creation of an electronic insulin diary system for recording the history of insulin doses delivered to the patient such as recording bolus injections and/or basal injections over time. The diary would record insulin related information including: basal and/or bolus dosage of insulin, type of insulin and concentration, time of administration, alerts to remind of timing of dosage. Alternatively, these data are sent directly to a software application without any user input or interaction. The diary may link to continuous glucose monitoring systems and/or blood glucose meters in real time or after a delay (asynchronously). The diary may be able to upload data to and/or download data from a cloud computing system for creating a record of insulin delivery that is portable across multiple computing devices. The electronic insulin diary may also share data in real time with care partners (parents, spouses, friends, caregivers, etc.), who act as a backup safety measure on dosing and glucose values/levels. The electronic insulin diary may also include a basal and/or bolus insulin calculator for calculating future insulin dose recommendations.

The record of the insulin taken by the patient may be automatically determined by the smart flange through recognition of the color code ring on the insulin vial. Insulin preparations fall into different types: Rapid-acting, short-acting, intermediate-acting, long-acting, and insulin mixtures. Different insulin types are labeled with different color-coded labels. The smart flange device and/or system may be configured to recognize and record insulin type by sensing the color code with a photocell, digital camera, or other electronic sensing element. The computing device may be configured with a barcode reader, QR code reader, or OCR character recognition software to directly read the label of the insulin vial. Alternatively, the user may manually enter the insulin type into the electronic insulin diary. The insulin diary may be used to inform and/or determine the patient's individual response to insulin doses and may be used to determine future insulin dose types, quantities, and/or frequency. The insulin diary software may be part of a system, which reads and records the patient's blood glucose levels from a glucose meter and determines the patient's insulin dosage requirements based on food intake, exercise, time of day, sleep or other parameters.

While the various systems and methods described herein depict injection systems having manually actuated plunger members, the injection data collection systems and methods described herein work equally well with automated or semi-automated injection systems such as injection pens.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject injection information collection procedures may be provided in packaged combination for use in executing such interventions. These supply "kits" may further include instructions for use and/or may be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for injection, comprising:

a syringe body having proximal and distal ends, a syringe interior, and a syringe flange at the proximal end thereof;

a stopper member disposed in the syringe interior;

a plunger member coupled to the stopper member and configured to be manipulated to insert the stopper member distally in the syringe interior relative to the syringe body;

a needle coupled to the syringe body at the distal end thereof; and a smart flange removably coupled to a syringe body, the smart flange comprising:

a mounting sensor to measure mounting data corresponding to a presence and a type of the syringe body disposed in the smart flange; and a processor to analyze the mounting data to determine the presence and the type of the syringe body disposed in the smart flange, wherein the mounting sensor comprises:

a contact member extending into a mounting space defined by the smart flange;

a mounting elongate member, wherein the contact member is coupled to a middle portion of the mounting elongate member;

a mounting magnetic member coupled to a distal end of the mounting elongate member; and a mounting magnetic sensor disposed adjacent the mounting magnetic member, wherein the contact member and the smart flange are configured such that disposing the syringe body in the mounting space of the smart flange moves the contact member relative to the smart flange, wherein the mounting elongate member and the contact member are configured such that moving the contact member relative to the smart flange elastically bends the mounting elongate member, wherein the mounting magnetic member and the mounting elongate member are configured such that elastically bending the mounting elongate member moves the mounting magnetic member relative to the mounting magnetic sensor, and wherein the mounting magnetic sensor detects movement of the mounting magnetic member and generates the mounting data based on the detected movement of the mounting magnetic member, wherein the mounting elongate member is elongated in a first direction perpendicular to a longitudinal axis of the plunger member corresponding to a movement of the plunger member to inject a fluid contained within the syringe interior, wherein the contact member is coupled to a middle portion of the mounting elongate member relative to the first direction, wherein the mounting elongate member and the contact member are configured such that moving the contact member relative to the smart flange elastically bends the mounting elongate member in a second direction perpendicular to both the first direction and the longitudinal axis, and wherein the mounting magnetic member and the mounting elongate member are configured such that elastically bending the mounting elongate member moves the mounting magnetic member relative to the mounting magnetic sensor in a third direction anti-parallel to the second direction.

2. The system of claim 1, where the plunger member has an X-shaped cross-section, wherein the smart flange defines a side-facing mounting opening, and wherein the smart flange comprises a pair of orientation ribs configured to orient the plunger member as it enters the side-facing mounting opening.

3. The system of claim 1, wherein the mounting magnetic sensor is a magnetoresistive angle sensor.

4. The system of claim 1, wherein the smart flange defines an internal space, and wherein the mounting elongate member, the mounting magnetic member, and the mounting magnetic sensor are disposed in the internal space.

5. The system of claim 1, the smart flange further comprising an injection sensor to measure injection data corresponding to a movement of the plunger member relative to the syringe body, wherein the processor analyzes the injection data to determine an occurrence of an injection event.

6. The system of claim 5, wherein the injection sensor comprises:

a wheel;

an injection elongate member coupled to the wheel and rotatably mounted to the smart flange;

an injection magnetic member coupled to a distal end of the injection elongate member; and an injection magnetic sensor disposed adjacent the injection magnetic member.

7. The system of claim 6, wherein the smart flange defines an internal space, and wherein the injection elongate member, the injection magnetic member, and the injection magnetic sensor are disposed in the internal space.

8. The system of claim 6, wherein the wheel and the smart flange are configured such that moving the plunger member axially relative to the smart flange rotates the wheel, wherein the injection elongate member and the wheel are configured such that rotating the wheel rotates the injection elongate member, wherein the injection magnetic member and the injection elongate member are configured such that rotating the injection elongate member rotates the injection magnetic member relative to the injection magnetic sensor, and wherein the injection magnetic sensor detects rotation of the injection magnetic member and generates the injection data based on the detected rotation of the injection magnetic member.

9. The system of claim 6, wherein the injection magnetic sensor is a magnetoresistive rotary sensor.

10. The system of claim 6, wherein the plunger member has an X-shaped cross-section and comprises four radially extending portions, wherein the wheel and the plunger member are configured such that the wheel contacts two of the four radially extending portions of the plunger member.

11. The system of claim 5, wherein the injection sensor comprises:

a roller rotatably mounted to the smart flange;

an injection magnetic member coupled to a distal end of the roller member; and an injection magnetic sensor disposed adjacent the injection magnetic member.

12. The system of claim 11, wherein the smart flange defines an internal space, and wherein the injection elongate member, the injection magnetic member, and the injection magnetic sensor are disposed in the internal space.

13. The system of claim 11, wherein the roller and the smart flange are configured such that moving the plunger member axially relative to the smart flange rotates the roller, wherein the injection magnetic member and the roller are configured such that rotating the roller rotates the injection magnetic member relative to the injection magnetic sensor, and wherein the injection magnetic sensor detects rotation of the injection magnetic member and generates the injection data based on the detected rotation of the injection magnetic member.

14. The system of claim 11, wherein the injection magnetic sensor is a magnetoresistive rotary sensor.

15. The system of claim 11, wherein the plunger member has an X-shaped cross-section and comprises four radially extending portions, wherein the roller and the plunger member are configured such that the roller contacts two of the four radially extending portions of the plunger member.

16. The system of claim 15, the smart flange comprising a pair of orientation ribs defining a mounting space sized to allow the smart flange to mount on the plunger member only with roller in contact with two of the four radially extending portions of the plunger member.

17. The system of claim 11, wherein the roller is suspended in the smart flange to accommodate a plurality of syringe bodies having respective different sizes.

18. The system of claim 5, wherein the injection sensor comprises:

a wheel; and an injection sensor disposed adjacent the wheel to measure a rotation of the wheel.

19. The system of claim 18, wherein the injection sensor is an optical sensor.

20. The system of claim 18, wherein the injection sensor is a capacitive sensor.

21. The system of claim 1, wherein the syringe body comprises a syringe flange, and wherein the smart flange comprises a plurality of snaps configured to releasably couple the smart flange to the syringe body.

22. The system of claim 1, wherein the syringe body has a volume selected from the group consisting of 0.3 ml, 0.5 ml, and 1 ml.

23. The system of claim 5, wherein the injection sensor comprises:

a plurality of rollers rotatably mounted to the smart flange;

a plurality of injection magnetic members coupled to respective distal ends of the plurality of roller members; and a plurality of injection magnetic sensors disposed adjacent respective injection magnetic members.

24. The system of claim 1, wherein the type of the syringe body disposed in the finger flange is a size of the syringe body, and wherein a degree of the bending of the mounting elongate member corresponds to the size of the syringe body.

25. A system for injection, comprising:

a syringe body having proximal and distal ends, a syringe interior, and a syringe flange at the proximal end thereof;

a stopper member disposed in the syringe interior;

a plunger member coupled to the stopper member and configured to be manipulated to insert the stopper member distally in the syringe interior relative to the syringe body;

a needle coupled to the syringe body at the distal end thereof; and a smart flange removably coupled to a syringe body, the smart flange comprising:

a sensor to measure data corresponding to a presence, a type of the syringe body disposed in the smart flange, and a movement of the plunger member relative to the syringe body; and a processor to analyze the data to determine the presence and the type of the syringe body disposed in the smart flange and an occurrence of an injection event, wherein the sensor comprises:

a wheel extending into a mounting space defined by the smart flange;

an elongate member, wherein a contact member is coupled to a middle portion of the elongate member;

a magnetic member coupled to a distal end of the elongate member; and a magnetic sensor disposed adjacent the magnetic member, wherein the elongate member is elongated in a first direction perpendicular to a longitudinal axis of the plunger member corresponding to a movement of the plunger member to inject a fluid contained within the syringe interior, wherein the contact member is coupled to a middle portion of the elongate member relative to the first direction, wherein the elongate member and the contact member are configured such that moving the contact member relative to the smart flange elastically bends the elongate member in a second direction perpendicular to both the first direction and the longitudinal axis, and wherein the magnetic member and the elongate member are configured such that elastically bending the elongate member moves the magnetic member relative to the magnetic sensor in a third direction anti-parallel to the second direction.

* * * * *